(12) United States Patent
Pho et al.

(10) Patent No.: US 12,220,221 B2
(45) Date of Patent: Feb. 11, 2025

(54) IDENTIFYING CONDITIONS USING RESPIRATION RATE

(71) Applicant: Oura Health Oy, Oulu (FI)

(72) Inventors: Gerald Pho, Somerville, MA (US); Kirstin Elizabeth Aschbacher, San Francisco, CA (US); Michael Chapp, Lafayette, CA (US); Harpreet Singh Rai, San Francisco, CA (US)

(73) Assignee: Oura Health Oy, Oulu (FI)

( * ) Notice: Subject to any disclaimer, the term of this patent is extended or adjusted under 35 U.S.C. 154(b) by 789 days.

(21) Appl. No.: 17/405,220

(22) Filed: Aug. 18, 2021

(65) Prior Publication Data

US 2022/0054040 A1 Feb. 24, 2022

Related U.S. Application Data

(60) Provisional application No. 63/067,588, filed on Aug. 19, 2020.

(51) Int. Cl.
*A61B 5/08* (2006.01)
*A61B 5/00* (2006.01)

(52) U.S. Cl.
CPC ......... *A61B 5/0816* (2013.01); *A61B 5/4812* (2013.01); *A61B 5/4815* (2013.01); *A61B 5/6826* (2013.01); *A61B 5/7275* (2013.01); *A61B 5/743* (2013.01)

(58) Field of Classification Search
CPC .......... A61B 5/121; A61B 5/12; A61B 5/123; A61B 5/128; A61B 5/38
See application file for complete search history.

(56) References Cited

U.S. PATENT DOCUMENTS

| | | | |
|---|---|---|---|
| 2007/0118054 A1* | 5/2007 | Pinhas | G16H 40/67 600/587 |
| 2012/0265080 A1* | 10/2012 | Yu | A61B 5/6893 600/509 |
| 2015/0230750 A1* | 8/2015 | McDarby | A61B 5/087 600/407 |
| 2017/0173262 A1* | 6/2017 | Veltz | G16H 20/17 |

* cited by examiner

*Primary Examiner* — Tse W Chen
*Assistant Examiner* — Michael A Catina
(74) *Attorney, Agent, or Firm* — Holland & Hart LLP

(57) ABSTRACT

Methods, systems, and devices for detection of medical conditions using respiration rate data are described. A method may include receiving physiological data associated with a user, the physiological data being continuously collected via a wearable device associated with the user, determining a set of respiration rate values for the user over a time interval based on the physiological data, and determining one or more respiration rate parameters associated with a change of the set of respiration rate values over the time interval. The method may further include determining one or more condition risk metrics associated with one or more medical conditions based on the one or more respiration rate parameters, where the one or more condition risk metrics associated with a relative probability that the user is associated with a respective medical condition.

12 Claims, 11 Drawing Sheets

IDENTIFYING CONDITIONS USING RESPIRATION RATE

CROSS REFERENCE

The present Application for Patent claims the benefit of U.S. Provisional Patent Application No. 63/067,588 by Aschbacher et al., entitled "IDENTIFYING CONDITIONS USING RESPIRATION RATE," filed Aug. 19, 2020, assigned to the assignee hereof, and expressly incorporated by reference herein.

FIELD OF TECHNOLOGY

The following relates to wearable devices and data processing, including techniques for identifying conditions using respiration rate.

BACKGROUND

Some wearable devices may be configured to collect physiological data from users, including temperature data, heart rate data, and the like. Many users have a desire for more insight regarding their physical health.

DETAILED DESCRIPTION

Figure 1:
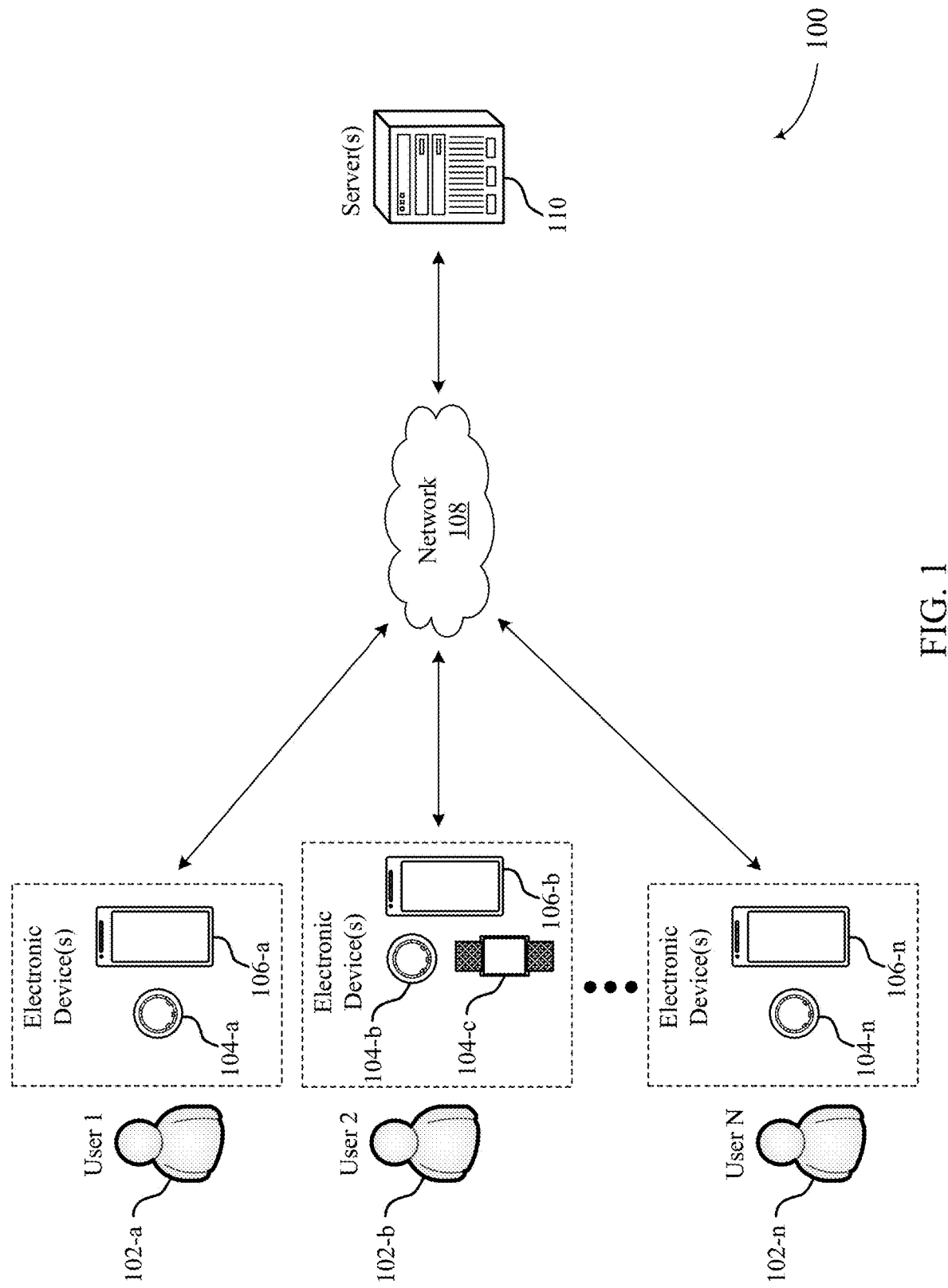
FIG. 1 illustrates an example of a system that supports identifying conditions using respiration rate in accordance with aspects of the present disclosure.

Some wearable devices may be configured to collect physiological data from users, including temperature data, heart rate data, and the like. Acquired physiological data may be used to analyze the user's movement and other activities, such as sleeping patterns. Many users have a desire for more insight regarding their physical health, including their sleeping patterns, activity, and overall physical well-being.

In some implementations, physiological data for a user may be used to identify certain medical conditions, such as illness, asthma, sleep apnea, and the like. However, many users may only have their physiological data checked a few times a year, such as when their temperature and blood pressure are taken during their annual medical checkup. These sparse, infrequent physiological data readings provide a very limited view into the user's overall health. Moreover, while some wearable devices are configured to collect physiological data from users, the data collected by the wearable devices is of limited value, and may not capture the full picture of the user's health. For example, some conventional wearable devices may determine a daily average temperature for a user. However, these daily averages may represent temperature data points which are temporally far apart, and may not be able to illustrate how the user's temperature fluctuates over smaller periods of time or throughout the day, which may provide valuable insight into the user's overall health.

Moreover, it has been found that a user's respiration rate may reflect a physiologic change and/or strain on the user's body, such as a change/strain on the user's cardiovascular and/or respiratory systems due to one or more user conditions/behaviors. However, many wearable devices do not continually track a user's respiration rate. Moreover, wearable devices which do track a user's respiration rate do not utilize a user's respiration rate to calculate scores for the user (e.g., sleep scores, readiness scores), and do not utilize a user's respiration rate to identify physiologic change on the user's body, such as an onset of certain medical conditions (e.g., onset of sleep deprivation)

Accordingly, aspects of the present disclosure are directed to techniques for detecting and predicting medical conditions based on a user's respiration rate. In particular, computing devices of the present disclosure may continually monitor a user's respiration rate throughout a 24-hour day, and may determine or predict whether a user is experiencing (or will experience) some medical conditions, such as sleep deprivation, sleep apnea, asthma, allergies, lung damage (e.g., lung damage attributable to viruses or infections such as COVID-19), and the like.

In some aspects, a wearable device (e.g., ring wearable device) may continuously collect physiological data from a user, and computing devices of the present disclosure (e.g., ring, other wearable device, user device, server) may determine the user's respiration rate over time based on the acquired physiological data. Subsequently, the computing devices may determine one or more respiration rate parameters for the user based on the respiration rate over time, and may determine whether the user is likely to be experiencing (or likely to experience in the future) one or more medical conditions based on the determined respiration rate parameters.

For example, a system of the present disclosure may measure a user's respiration rate during a night of sleep, and may determine respiration rate parameters associated with the night of sleep. Example respiration rate parameters may include, but are not limited to, respiration rate at the start of sleep, respiration rate at the end of sleep, a difference between a starting respiration rate and an ending respiration rate, a slope of a line/curve fitted to the respiration rate over the night of sleep, a relationship of the user's respiration rate with classified sleep stages (e.g., relationship between respiration rate and transitions between different types of sleep), and the like. The system may then determine condition risk metrics associated with one or more medical conditions (e.g., sleep deprivation, sleep apnea, asthma) based on the respiration rate parameters, where the condition risk metrics are associated with a relative probability that the user is experiencing (or will experience) the respective medical conditions. The system may then report the determined condition risk metrics to the user, which may provide the user with a more comprehensive view of their sleeping patterns and overall health.

Aspects of the disclosure are initially described in the context of systems supporting physiological data collection from users via wearable devices. Additional aspects of the disclosure are described in the context of example respiration rate diagrams and an example GUI. Aspects of the disclosure are further illustrated by and described with reference to apparatus diagrams, system diagrams, and flowcharts that relate to identifying conditions using respiration rate.

FIG. 1 illustrates an example of a system 100 that supports identifying conditions using respiration rate in accordance with aspects of the present disclosure. The system 100 includes a plurality of electronic devices (e.g., wearable devices 104, user devices 106) which may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, which may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-a (User 1) may operate, or may be associated with, a wearable device 104-a (e.g., ring 104-a) and a user device 106-a that may operate as described herein. In this example, the user device 106-a associated with user 102-a may process/store physiological parameters measured by the ring 104-a. Comparatively, a second user 102-b (User 2) may be associated with a ring 104-b, a watch wearable device 104-c (e.g., watch 104-c), and a user device 106-b, where the user device 106-b associated with user 102-b may process/store physiological parameters measured by the ring 104-b and/or the watch 104-c. Moreover, an nth user 102-n (User N) may be associated with an arrangement of electronic devices described herein (e.g., ring 104-n, user device 106-n). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more LEDs (e.g., red LEDs, green LEDs) which emit light on the palm-side of a user's finger to collect physiological data based on arterial blood flow within the user's finger. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices which utilize LEDs which are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-a associated with the first user 102-a may be communicatively coupled to the user device 106-a, where the user device 106-a is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time during which a user 102 is asleep, and classify periods of time during which the user 102 is asleep into one or more sleep stages (e.g., sleep stage classification). For example, as shown in FIG. 1, User 102-a may be associated with a wearable device 104-a (e.g., ring 104-a) and a user device 106-a. In this example, the ring 104-a may collect physiological data associated with the user 102-a, including temperature, heart rate, HRV, respiration rate, and the like. In some aspects, data collected by the ring 104-a may be input to a machine learning classifier, where the machine learning classifier is configured to determine periods of time during which the user 102-a is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-a via a GUI of the user device 106-a. Sleep stage classification may be used to provide feedback to a user 102-a regarding the user's sleeping patterns, such as recommended bedtimes, recommended wake-up times, and the like. Moreover, in some implementations, sleep stage classification techniques described herein may be used to calculate scores for the respective user, such as sleep scores, readiness scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, which repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-a via the wearable device 104-a. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models which are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g., in a hypothetical culture with 12 day "weeks", 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for detecting and predicting medical conditions based on data collected by a wearable device. In particular, the system 100 illustrated in FIG. 1 may support techniques for identifying a likelihood/probability that a user 102 is experiencing, or will experience, a medical condition based on the user's respiration rate, and causing a user device 106 corresponding to the user 102 to display an indication of the relative likelihood/probabilities of the respective medical conditions.

For example, as shown in FIG. 1, a ring 104-a corresponding to the user 102-a (User 1) may continuously collect physiological data from the user 102-a throughout the day. Subsequently, the ring 104-a, user device 106-a, and/or server 110 may determine respiration rate values for the user 102-a based on the acquired physiological data. For instance, the system 100 may determine the user's 102-a respiration rate at a regular or irregular periodicity, such as one respiration rate value per minute, per five minutes, per thirty seconds, and the like.

The system 100 (e.g., ring 104-a, user device 106-a, servers 110) may then determine respiration rate parameters associated with the user 102-a over some time period, such as night of sleep. Example respiration rate parameters may include, but are not limited to, respiration rate at the start of sleep, respiration rate at the end of sleep, a difference between a starting respiration rate and an ending respiration rate, a slope of a line/curve fitted to the respiration rate over the night of sleep, a relationship of the user's respiration rate with classified sleep stages (e.g., average respiration rate within classified sleep stages, or average respiration rate at transitions between sleep stages), and the like. The system 100 may then determine condition risk metrics associated with one or more medical conditions (e.g., sleep deprivation, sleep apnea, asthma) based on the respiration rate parameters, where the condition risk metrics are associated with a relative probability that the user 102-a is experiencing (or will experience) the respective medical conditions. The system 100 may then report the determined condition risk metrics to the user, which may provide the user with a more comprehensive view of their sleeping patterns and overall health.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
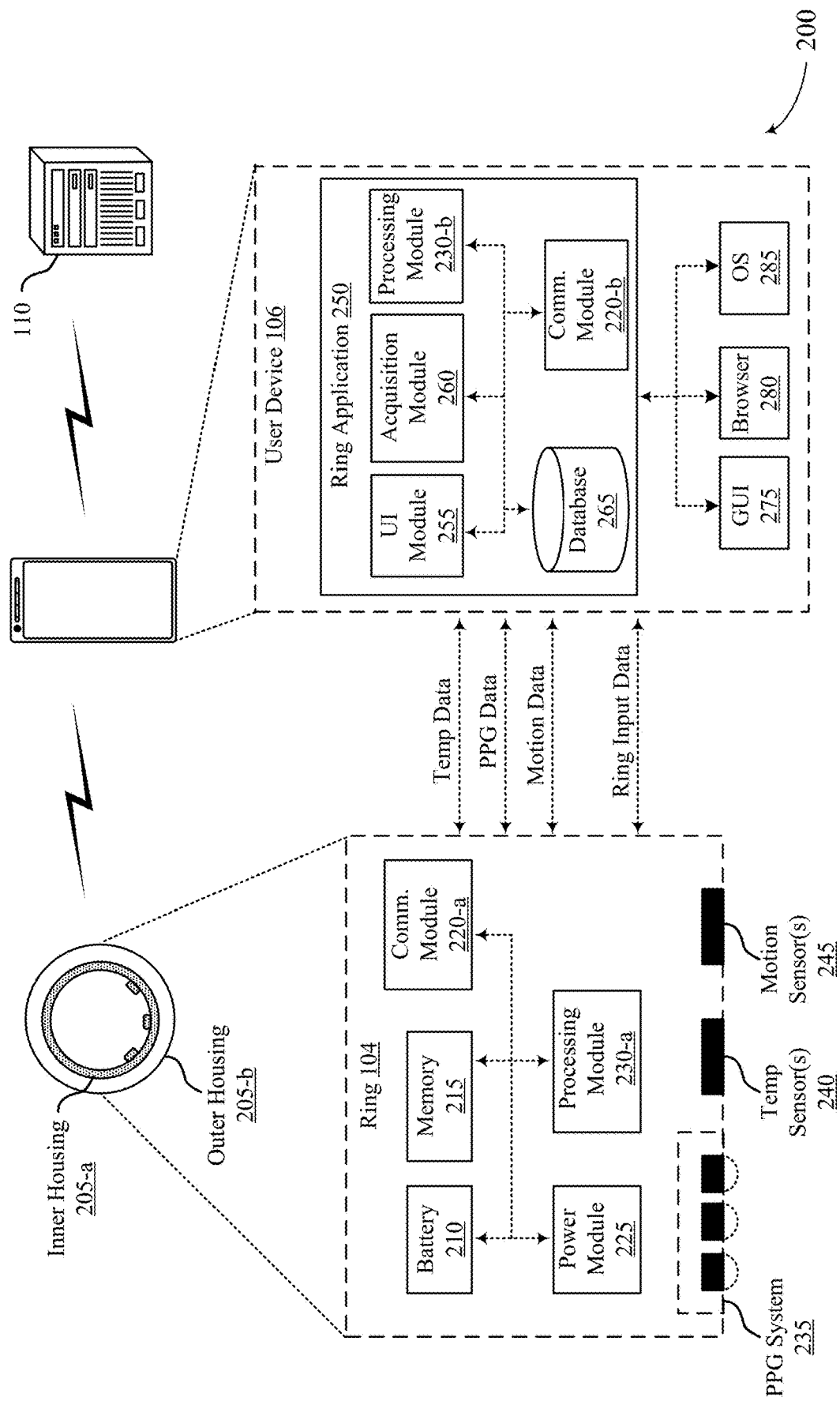
FIG. 2 illustrates an example of a system that supports identifying conditions using respiration rate in accordance with aspects of the present disclosure.

FIG. 2 illustrates an example of a system 200 that supports identifying conditions using respiration rate in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiration rate, heart rate, HRV, blood oxygen levels, and the like.

System 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205, which may include an inner housing 205-a and an outer housing 205-b. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-a, a memory 215, a communication module 220-a, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components which are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated.

In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-b component (e.g., a shell) and an inner housing 205-a component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-b (e.g., a metal outer housing 205-b). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-b may be fabricated from one or more materials. In some implementations, the outer housing 205-b may include a metal, such as titanium, which may provide strength and abrasion resistance at a relatively light weight. The outer housing 205-b may also be fabricated from other materials, such polymers. In some implementations, the outer housing 205-b may be protective as well as decorative.

The inner housing 205-a may be configured to interface with the user's finger. The inner housing 205-a may be formed from a polymer (e.g., a medical grade polymer) or other material. In some implementations, the inner housing 205-a may be transparent. For example, the inner housing 205-a may be transparent to light emitted by the PPG light emitting diodes (LEDs). In some implementations, the inner housing 205-a component may be molded onto the outer housing 205-a. For example, the inner housing 205-a may include a polymer that is molded (e.g., injection molded) to fit into an outer housing 205-b metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-a of the ring 104 may include one or more processors (e.g., processing units), microcontrollers, digital signal processors, systems on a chip (SOCs), and/or other processing devices. The processing module 230-a communicates with the modules included in the ring 104. For example, the processing module 230-a may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-a may communicate with the memory 215. The memory 215 may include computer-readable instructions that, when executed by the processing module 230-a, cause the processing module 230-a to perform the various functions attributed to the processing module 230-a herein. In some implementations, the processing module 230-a (e.g., a microcontroller) may include additional features associated with other modules, such as communication functionality provided by the communication module 220-a (e.g., an integrated Bluetooth Low Energy transceiver) and/or additional onboard memory 215.

The communication module 220-a may include circuits that provide wireless and/or wired communication with the user device 106 (e.g., communication module 220-b of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors which may be used to collect data in addition to, or which supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during 104 charging. The power module 225 may also regulate voltage (s) of the device electronics, regulate power output to the device electronics, and monitor the state of charge of the battery 210. In some implementations, the battery 210 may include a protection circuit module (PCM) that protects the battery 210 from high current discharge, over voltage during 104 charging, and under voltage during 104 discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240. The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during 104 exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-a near the user's finger. In some implementations, the temperature sensors 240 may be stand-alone temperature sensors 240. Additionally or alternatively, one or more temperature sensors 240 may be included with other components (e.g., packaged with other components), such as with the accelerometer and/or processor.

The processing module 230-a may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-a may sample the sensors at different rates and average/store different values for the different sensors. In some implementations, the processing module 230-a may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-a may sample the PPG signal and determine a user's pulse waveform based on the PPG signal. The processing module 230-a may determine a variety of physiological parameters based on the user's pulse waveform, such as a user's respiration rate, heart rate, HRV, oxygen saturation, and other circulatory parameters.

In some implementations, the PPG system 235 may be configured as a reflective PPG system 235 in which the optical receiver(s) receive transmitted light that is reflected through the region of the user's finger. In some implementations, the PPG system 235 may be configured as a transmissive PPG system 235 in which the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-a may control one or both of the optical transmitters to transmit light while sampling the PPG signal generated by the optical receiver. In some implementations, the processing module 230-a may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform, which may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-a may store the pulse waveform in memory 215 in some implementations. The processing module 230-a may process the pulse waveform as it is generated and/or from memory 215 to determine user physiological parameters described herein.

The processing module 230-a may determine the user's heart rate based on the pulse waveform. For example, the processing module 230-a may determine heart rate (e.g., in beats per minute) based on the time between peaks in the pulse waveform. The time between peaks may be referred to as an interbeat interval (IBI). The processing module 230-a may store the determined heart rate values and IBI values in memory 215.

The processing module 230-a may determine HRV over time. For example, the processing module 230-a may determine HRV based on the variation in the IBIs. The processing module 230-a may store the HRV values over time in the memory 215. Moreover, the processing module 230-a may determine the user's respiration rate over time. For example, the processing module 230-a may determine respiration rate based on frequency modulation, amplitude modulation, or baseline modulation of the user's IBI values over a period of time. Respiration rate may be calculated in breaths per minute or as another breathing rate (e.g., breaths per 30 seconds). The processing module 230-a may store user respiration rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BMI160 inertial micro electro-mechanical system (MEMS) sensor that may measure angular rates and accelerations in three perpendicular axes.

The processing module 230-a may sample the motion signals at a sampling rate (e.g., 50 Hz) and determine the motion of the ring 104 based on the sampled motion signals. For example, the processing module 230-a may sample acceleration signals to determine acceleration of the ring 104. As another example, the processing module 230-a may sample a gyro signal to determine angular motion. In some implementations, the processing module 230-a may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiration rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a sleep score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-a may compress the data stored in memory 215. For example, the processing module 230-a may delete sampled data after making calculations based on the sampled data. As another example, the processing module 230-a may average data over longer periods of time in order to reduce the number of stored values. In a specific example, if average temperatures for a user over one minute are stored in memory 215, the processing module 230-a may calculate average temperatures over a five minute time period for storage, and then subsequently erase the one minute average temperature data. The processing module 230-a may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during 104 portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") which may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-*b*, a communication module 220-*b*, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations which require relatively low processing power and/or operations which require a relatively low latency, whereas the user device 106 may transmit the data to the servers 110 for processing operations which require relatively high processing power and/or operations which may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., sleep score, readiness score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, sleep scores, readiness scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner which is consistent with their sleep schedules. In some cases, users may be able to selectively adjust (e.g., via the GUI) a timing of sleep days relative to calendar days so that the sleep days are aligned with the duration of time in which the respective users typically sleep.

In some implementations, each overall score for a user for each respective day (e.g., sleep score, readiness score) may be determined/calculated based on one or more "contributors," "factors," or "contributing factors." For example, a user's overall sleep score may be calculated based on a set of contributors, including: total sleep, efficiency, restfulness, REM sleep, deep sleep, latency, timing, or any combination thereof. The sleep score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall readiness score may be calculated based on a set of contributors, including: sleep, sleep balance, heart rate, HRV balance, recovery index, temperature, activity, activity balance, or any combination thereof. The readiness score may include any quantity of contributors. The "sleep" contributor may refer to the combined sleep score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the readiness score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the respective devices of the system 200 may support techniques for detecting and predicting medical conditions based on data collected by a wearable device. In particular, the system 200 illustrated in FIG. 2 may support techniques for identifying a likelihood/probability that a user 102 is experiencing, or will experience, a medical condition based on the user's respiration rate, and causing the user device 106 corresponding to the user 102 to display an indication of the relative likelihood/probabilities of the respective medical conditions.

For example, the ring 104 of the system 200 may continuously collect physiological data from the user throughout the day. Subsequently, the components of the system 200 (e.g., ring 104, user device 106, and/or server 110) may determine respiration rate values for the user based on the acquired physiological data. For instance, the system 200 may determine respiration rate values for the user at a regular or irregular periodicity, such as one respiration rate value per minute, per five minutes, and the like. In some cases, the system 200 may determine the user's respiration rate based on modulations or fluctuations in the user's heart rate (or HRV) over time. In particular, the system 200 may determine heart rate data for the user based on acquired physiological data, and may determine amplitude modulation data of the heart rate data (e.g., amplitude modulation of a PPG signal), frequency modulation data of the heart rate data (e.g., frequency modulation of the PPG signal or detected inter-beat-intervals, or IBIs), or both. The system 200 may then utilize the amplitude modulation data, the frequency modulation data, or both, to determine the user's respiration rate.

The system may perform both amplitude and frequency extraction procedures of the user's PPG signal to determine both amplitude and frequency modulation data, and may then perform mathematical procedures, such as linear combination procedures, to combine the amplitude and frequency modulation data to determine respiration rate data. In some implementations, the system 200 may utilize classifiers (e.g., machine learning classifiers or other algorithms) to determine which users have reliable amplitude modulation data, frequency modulation data, or both. In such cases, the system 200 may PPG data for each user into a classifier, where the classifier may determine user-specific weights for the respective amplitude and frequency modulation data in order to determine the respiration rate data for each user. In additional or alternative implementations, the system 200 may omit, reject, or otherwise ignore one of the amplitude modulation data and the frequency modulation data when determining the respiration rate data if the amplitude and modulation data are not in line with one another (e.g., if they are far away from one another). In such cases, the system 200 may utilize one of the amplitude or frequency modulation data which is closer to the respective expected values in order to determine the user's respiration rate data, and may omit or discard the other, noisier modulation data.

In some cases, the ring 104 may enable tighter and more direct contact with the user's finger as compared to other wearable devices (e.g., watch wearable devices), which may reduce noise and result in more accurate physiological data collection. Moreover, the ring 104 may measure arterial blood flow (as opposed to capillary blood flow or flow through veins), which may provide stronger readings and further improve the signals acquired by the ring 104, and therefore improve physiological data collection. The positioning of the sensors on the lower inner surface of the ring, allowing for the capture of data from arterial blood flow to the underside of the user's finger via the user's wrist and palm, may also contribute to more accurate physiological data collection, based in part on the lesser pigmentation present in the palm of users' skin, as compared to the top of users' hands or wrists, for example. Taken together, the ring 104 may collect higher-quality and more accurate physiological data as compared to other wearable devices, which may result in more accurate heart rate measurements, and more accurate determination of frequency modulation data, thereby leading to improved respiration rate determination. In turn, the improved respiration rate determination capabilities of the system 200 may enable the system 200 to perform additional functions which may not be performed by other systems or other wearable devices, such as the determination of medical conditions based on respiration rate, as described herein.

Indeed, it has been found that the system 200 is able to measure respiration rate for a user with similar accuracy as respiration rate values derived from an electrocardiogram (ECG) device. To validate these findings, a user's respiration rate was monitored using a ring wearable device (e.g., ring 104), and compared to respiration rate values which were derived from ECG modulations (e.g., an algorithm which derives respiration rate values from ECG). Comparing the respiration rate data generated by the ring 104/system 200 and the ECG device, it was found that the respiration rate data generated by the ring 104 closely tracks respiration rate data generated by the ECG device across all measurement points in a single sleep (e.g., overnight). This indicates that the ring 104 and system 200 may provide a highly accurate representation of a user's respiration rate over a period of time (e.g., overnight).

Respiration rate values which are collected/determined by the system 200 may be further shown and described with reference to FIG. 3.

Figure 3:
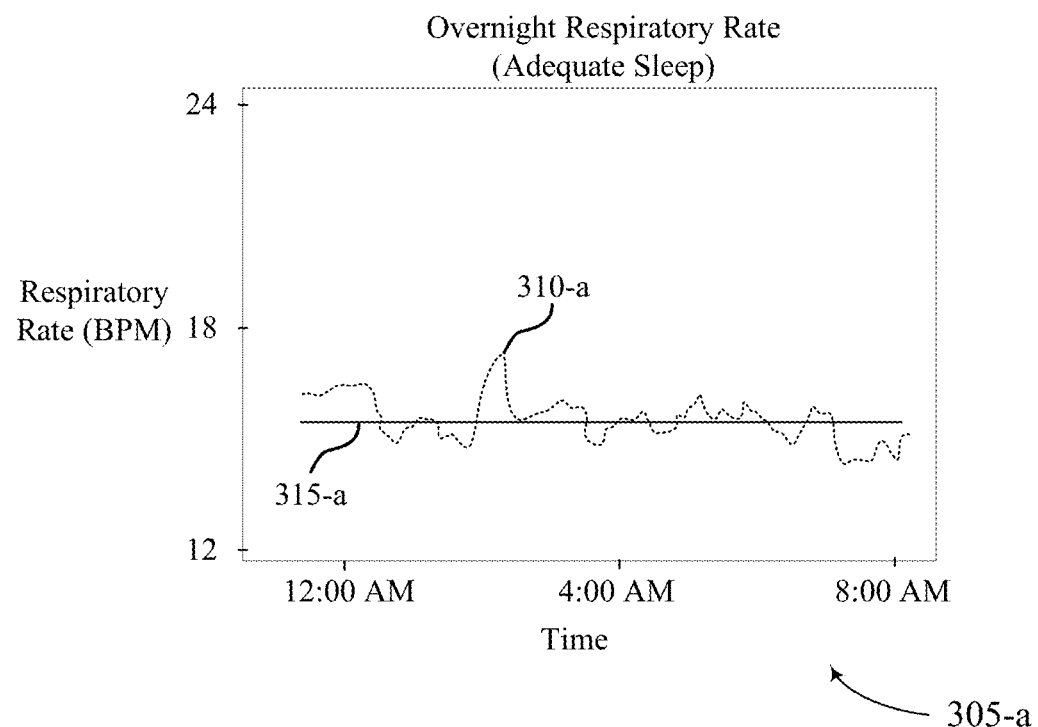
FIG. 3 illustrates an example of a respiration rate diagram that supports identifying conditions using respiration rate in accordance with aspects of the present disclosure.
Figure 3:
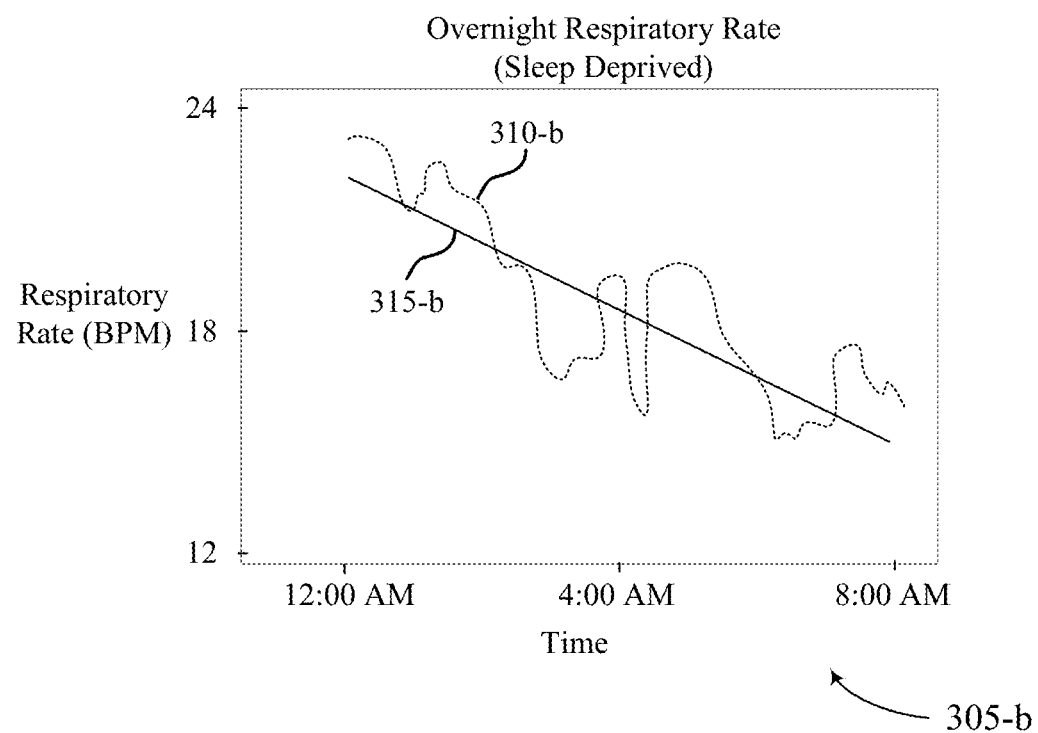

FIG. 3 illustrates an example of a respiration rate diagram 300 that supports identifying conditions using respiration rate in accordance with aspects of the present disclosure. Aspects of the respiration rate diagram 300 may implement, or be implemented by, aspects of the system 100, system 200, or both. For example, in some implementations, the respiration rate diagram 300 illustrates data (e.g., respiration rate values) for a user which are collected or determined by the system 100, the system 200, or both. Additionally or alternatively, respiration rate graphs 305-*a* and 305-*b* of the respiration rate diagram 300 may include examples of graphs which may be displayed to a user via the GUI 275 of the user device 106, as shown in FIG. 2.

The respiration rate diagram 300 includes a first respiration rate graph 305-*a* and a second respiration rate graph 305-*b* which illustrate a user's respiration rate over time. For example, the curves 310-*a* and the curve 310-*b* of the first respiration rate graph 305-*a* and the second respiration rate graph 305-*b*, respectively, illustrate a change in a user's (or multiple users') respiration rates over the course of a night of sleep for the respective user(s). The x-axes of the respiration rate graphs 305 illustrate time over the course of a night of sleep (e.g., 12:00 AM-8:00 AM), and the y-axes of the respiration rate graphs 305 illustrate the respective user's respiration rate in breaths per minute (breath/min). In particular, as will be discussed in further detail herein, the first respiration rate graph 305-*a* illustrates overnight respiration rate for a user that has had adequate sleep over one or more previous/consecutive nights (e.g., a user who had 8-9 hours of sleep), whereas the second respiration rate graph 305-*b* illustrates overnight respiration rate for a user that has had inadequate sleep over one or more previous/consecutive nights (e.g., a user who had less than 8 hours of sleep).

In some aspects, upon determining respiration rate values for a user over some time interval (e.g., 24-hour day, 24-hour sleep day, a night of sleep), as illustrated in respiration rate graphs 305, the components of the system 200 may then determine respiration rate parameters associated with the user based on the respiration rate data/values for the user. For example, the components of the system 200 may determine one or more respiration rate parameters associated with each night of sleep for the user. In some implementations, the system 200 may additionally or alternatively determine one or more respiration rate parameters over multiple nights of sleep.

In some aspects, respiration rate parameters may be associated with a change of the user's respiration rate over the course of the respective time interval. Example respiration rate parameters may include, but are not limited to: 1) starting respiration rate at a beginning of the time interval, 2) ending respiration rate at an end of the time interval, 3) total drop in respiration rate (e.g., total drop overnight), 4) parameters of a line/curve fit to the user's respiration rate values (e.g., slope of the line), 5) maximum respiration rate, 6) minimum respiration rate, 7) difference between maximum and minimum respiration rates, 8) a relationship of the user's respiration rate with classified sleep stages (e.g., relationship between respiration rate and transitions between different types of sleep), and the like. For example, respiration rate parameters may include a rate of change of a user's respiration rate values over a time interval (e.g., over a night of sleep), a total change in the respiration rate values over the time interval, a relationship between the respiration rate values and one or more classified sleep periods for the user within the time interval, or any combination thereof.

Additionally or alternatively, respiration rate parameter values may also include values associated with deviations in respiration rate parameters, such as deviations from average/baseline respiration rate parameter values, or any other respiration rate parameter values. Moreover, examples of multi-night respiration rate parameters may include averages of the respiration rate parameter values from multiple nights, and baseline values of the respiration rate parameters over multiple nights.

In particular, as described previously herein, it has been found that a user's respiration rate may reflect a physiologic change and/or strain on the user's body, such as a change/strain on the user's cardiovascular and/or respiratory systems due to one or more user conditions/behaviors. As such, the system 200 may be configured to determine respiration rate parameters for the user that may be indicative of one or more medical conditions or user conditions/behaviors that the user may be experiencing, such as sleep deprivation or insufficient restorative sleep (from a physiologic perspective).

In some implementations, the respective devices of the system 200 may determine respiration rate parameters based on changes in a user's respiration rate throughout some time period (e.g., night of sleep). For example, as shown in FIG. 3, the system 200 may track a user's respiration rate (e.g., respiration rate values) throughout a night of sleep, as shown via curves 310-*a* and 310-*b*. In some aspects, the system 200 may fit a line (e.g., best fit line, regression trend line, linear regression line) to the respiration rate values for the user over the time interval. For instance, the system 200 may fit a line 315-*a* to the curve 310-*a*, and may fit a line 315-*b* to the curve 310-*b*. The system 200 may use any techniques to fit the lines 315 to the respective curves, including standard linear regression or robust Huber regression techniques. In some cases, the system 200 may filter the respiration rate values (e.g., filter the values of the curves 310) in order to remove outliers prior to fitting the respective lines 315. In a specific example, the computing device may determine a change in respiration rate during sleep by calculating a slope of a best fit line though the respiration rate data (e.g., a regression trend line). Although FIG. 3 illustrates linear trend lines 315, other trend lines 315 with other defining values may be fitted to the respiration rate data.

In some cases, the system 200 may determine respiration rate parameters based on the lines 315 fitted to the user's respiration rate values over the time interval. For example, the system 200 may determine a slope of the respective lines 315, where the slopes indicate a relative change in the user's respiration rate during sleep (e.g., slope of decline in the respiration rate). In this regard, example respiration rate parameters determined based on the fitted lines 315 may include whether there is a decline in the lines 315, and the rate of decline (e.g., slope). In some implementations, the computing device may determine the change in respiration rate during sleep by determining a difference in a starting respiration rate (e.g., at sleep onset) and an ending respiration rate (e.g., at waking).

In some examples described herein, a change in the user's respiration rate overnight (e.g., slope of the line 315) may indicate that the user is sleep deprived (e.g., sleep deprived at the start of sleep). In other words, respiration rate parameters associated with a user's respiration rate during sleep may be used to detect sleep deprivation or other physiological conditions.

For instance, as shown in FIG. 3, it has been found that users who are experiencing normal or adequate sleep (e.g., users who are not sleep deprived) exhibit relatively stable/constant respiration rates throughout a night of sleep. As such, users experiencing adequate sleep may be associated with relatively flat lines 315 (e.g., lines 315 with a slope above some threshold and/or close to zero), as shown in the line 315-*a* of the graph 305-*a*. As such, identification of relatively stable respiration rates (e.g., identification of little to no slope within line 315-*a*) may indicate that the user is not sleep deprived.

Comparatively, it has been found that users who are experiencing sleep deprivation exhibit elevated respiration rates at the start of sleep, and experience decreasing respiration rates over the course of a night of sleep. As such, users experiencing sleep deprivation may be associated with lines 315-*b* with declining slopes, as shown in the line 315-*b* of the respiration rate graph 305-*b*. In other words, users who are sleep deprived may exhibit an elevated starting respiration rate value (e.g., at 12:00 AM) at the start of sleep, where the user's respiration rate decreases over time while the user is sleeping. As such, the identification of a declining respiration rate (e.g., slope of line 315-*b* being less than some threshold slope) may indicate that a user may be sleep deprived. In some implementations, the computing devices may determine multi-night parameters based on the line 315 in the respiration rate values, such as average slope values, baseline slope values, and deviations in slope values.

As another example, the system 200 may determine that the user may be sleep deprived if a slope in respiration rate (e.g., slope of line 315-*b*) is newly detected or increasing in value during subsequent nights, assuming such a slope was not present in prior nights or was only barely present (e.g., less than a threshold level). In some cases, sleep deprivation may be indicated by the elevated starting respiration rate, where the slope to a lower ending respiration rate indicates potential recovery.

In some aspects, the system 200 may be configured to determine and/or adjust scores (e.g., sleep scores, readiness scores) for the user based on the user's respiration rate values and/or respiration rate parameters. For example, as noted previously herein, a user's overall sleep score may be calculated based on a set of contributors, including: total sleep, efficiency, restfulness, REM sleep, deep sleep, latency, timing, or any combination thereof. In some aspects, the system 200 may additionally or alternatively utilize respiration rate data (e.g., respiration rate values, respiration rate parameters) to calculate the user's sleep score and/or readiness score. In other words, the system 200 may utilize a user's respiration rate data as an additional contributor or contributing factor to the determination of the user's sleep scores and/or readiness scores. By including respiration rate data within the sets of contributing factors used to determine scores for the user, the system 200 may enable a more direct determination of the user's sleep and readiness scores based on respiration rate (as opposed to an indirect determination in which respiration rate is taken into account when determining one of the individual contributing factors such as sleep stages).

After identification of respiration rate parameters, the system 200 may then determine condition risk metrics associated with one or more medical conditions (e.g., sleep deprivation, sleep apnea, asthma) based on the respiration rate parameters, where the condition risk metrics are associated with a relative probability that the user 102-*a* is experiencing (or will experience) the respective medical conditions.

Medical conditions which may be determined/predicted based on the user's respiration rate and/or respiration rate parameters may include, but are not limited to, sleep deprivation, sleep apnea, asthma, allergies, chronic obstructive pulmonary disease (COPD), respiratory infections or viruses such as flu or coronavirus (e.g., COVID-19), other lung-related conditions (e.g., lung damage from diseases such as Long COVID), or other health conditions. For example, in some cases, the system 200 may determine respiration rate parameters that are indicative of user sleep deprivation and/or sustained periods of mental or psychological stress. In some implementations, the computing devices may identify potential conditions by using the respiration rate parameters alone. In other implementations, the computing devices may use the respiration rate parameters along with other measured physiological parameters (e.g., heart rate and/or temperature) to identify and/or confirm potential conditions.

For example, referring to respiration rate graph 305-*b* illustrated in FIG. 3, the system 200 may determine a slope of a user's respiration rate values over a time interval (e.g., slope of line 315-*b*), and may determine condition risk metrics based on the determined slope. In particular, the system 200 may compare the determined slope to one or more threshold slope values, and may determine condition risk metrics based on the comparison. For instance, if the slope is above a threshold slope value (e.g., line 315-*b* is flatter than a threshold line), the system 200 may generate a first condition risk metric indicating that it is unlikely that the user is sleep deprived. Comparatively, if the slope is below the threshold slope value (e.g., line 315-*b* is steeper than the threshold line), the system 200 may generate a second condition risk metric indicating that it is more likely that the user is sleep deprived. In this regard, the system 200 may use the determined slope of the line 315-*b* to determine relative probabilities that the user is suffering from sleep deprivation.

A change in a user's respiration rate values over a time interval may also be illustrated as a total change in the user's respiration rate over the time interval. This may be further shown and described with reference to FIG. 4.

Figure 4:
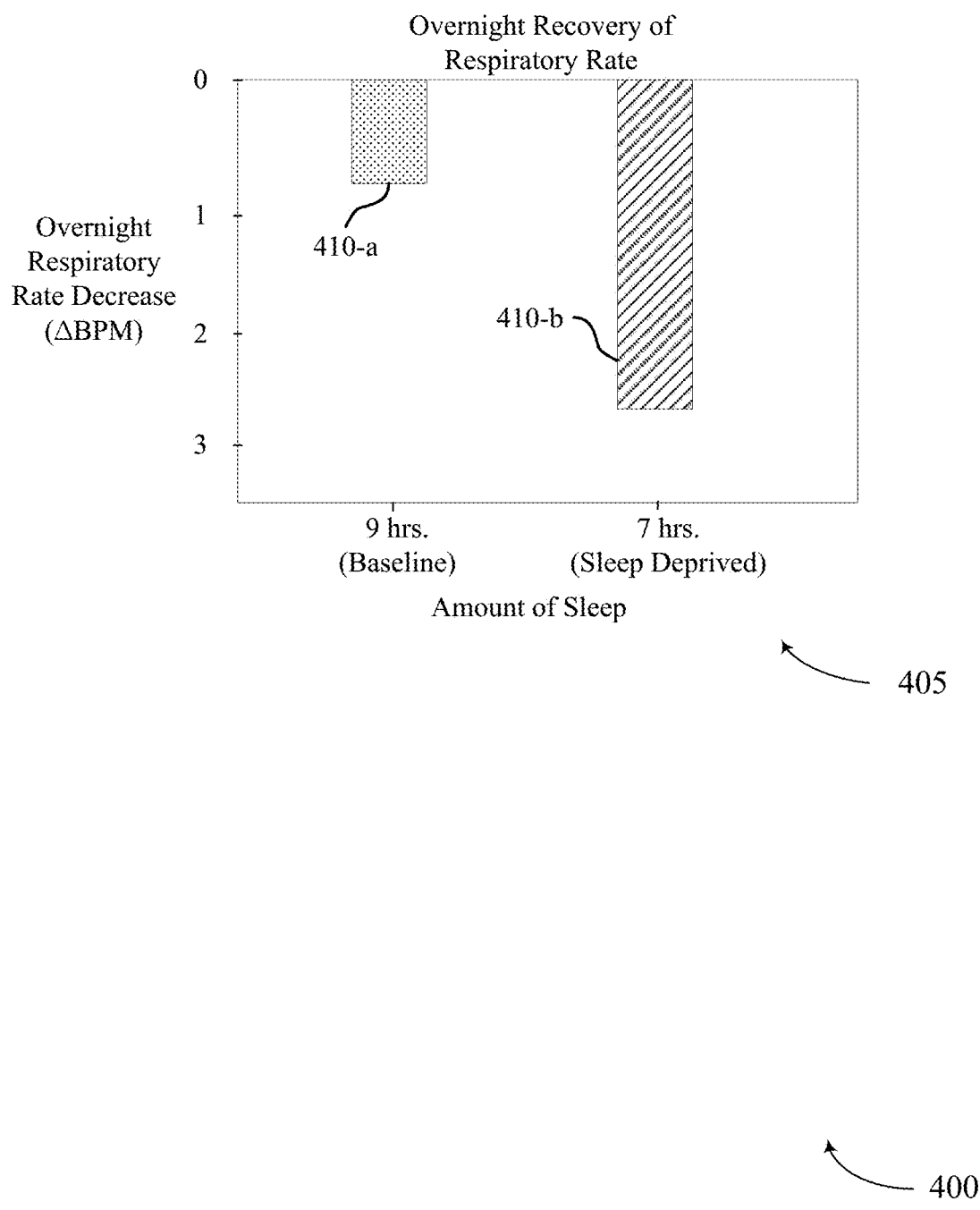
FIG. 4 illustrates an example of a respiration rate diagram that supports identifying conditions using respiration rate in accordance with aspects of the present disclosure.

FIG. 4 illustrates an example of a respiration rate diagram 400 that supports identifying conditions using respiration rate in accordance with aspects of the present disclosure. Aspects of the respiration rate diagram 400 may implement, or be implemented by, aspects of the system 100, system 200, or both. For example, in some implementations, the respiration rate diagram 400 illustrates data (e.g., respiration rate values, respiration rate parameters) for a user which are collected or determined by the system 100, the system 200, or both. Additionally or alternatively, respiration rate graphs 405 may include an example of a graph which may be displayed to a user via the GUI 275 of the user device 102, as shown in FIG. 2.

Graph 405 illustrated in FIG. 4 shows an overnight change (e.g., decrease) in a user's respiration rate values. In other words, the graph 405 shows an overnight recovery (overnight decrease) in a user's respiration rate, or an average respiration rate across multiple users. Specifically, bar 410-*a* illustrates a decrease in respiration rate for a user that has had adequate sleep (e.g., 9 hours/night) for one or more previous nights, whereas bar 410-*b* illustrates the decrease in respiration rate for a user that is sleep deprived (e.g., 7 hours/night) for one or more previous nights. As shown in graph 405, the overnight decrease in respiration rate is larger for the sleep deprived user (e.g., 2 breath/min or greater) than for the user with adequate sleep (e.g., <1 breath/min). In other words, sleep deprived users exhibit greater decreases in their overnight respiration rates as compared to users who are not sleep deprived.

Accordingly, in some cases, the system 200 may utilize overnight respiration rate recovery metrics, such as total change in respiration rate values over time or a difference between maximum and minimum respiration rates within the time interval, as respiration rate parameters for determining condition risk metrics. For instance, if a user exhibits an overnight respiration rate decrease which is less than a threshold (e.g., bar 410-*a*), the system 200 may determine a first condition risk metric indicating a smaller probability that the user is sleep deprived. Comparatively, if a user exhibits an overnight respiration rate decrease which is greater than a threshold (e.g., bar 410-*b*), the system 200 may determine a second condition risk metric indicating a larger probability that the user is sleep deprived.

As noted previously herein, in some aspects, the system 200 may generate the condition risk metrics solely based on respiration rate values and/or respiration rate parameters for the user. In additional or alternative implementations, the system 200 may generate the condition risk metrics based on respiration rate values/parameters and other physiological data collected via the ring 104, such as heart rate data, HRV data, temperature data, and the like. In other words, the system 200 may evaluate whether a user is experiencing (or will experience) medical conditions based on both respiration rate data and other physiological data parameters (e.g., HRV, temperature, blood oxygen levels).

In some implementations, the system 200 may utilize classifiers (e.g., machine learning classifiers) to determine respiration rate parameters and/or condition risk metrics for a user. In particular, the system 200 may train a classifier to determine condition risk metrics for a user based on inputted physiological data (e.g., respiration rate data) for the user. For example, in some cases, respiration rate values, respiration rate parameters (e.g., slope, total change), other physiological data, or any combination thereof, collected from a user may be inputted into a classifier (e.g., machine learning classifier), where the classifier is configured to determine condition risk metrics based on the received data.

In some implementations, user inputs received from a user (e.g., via GUI 275 of the user device 106) may be used to further train a classifier to identify condition risk metrics. In other words, a user may be able to generate user inputs which may then be used to train the machine learning classifier. For example, the classifier may identify/predict that a user is suffering from allergies based on received respiration rate values and/or respiration rate parameters. In other words, the classifier may generate a condition risk metric which is associated with a relatively high probability that the user is suffering from allergies. Subsequently, the system 200 may prompt the user (e.g., via the GUI 275) to confirm or deny whether the user is suffering from allergies, and the user inputs (e.g., confirmation or denial of allergy symptoms) may be used to further train the classifier to become more effective at accurately determining condition risk metrics (more accurate at identifying/predicting medical conditions based on respiration rate data).

Moreover, in some cases, the system 200 may be configured to determine condition risk metrics for a user (e.g., identify/predict medical conditions) by comparing a user's respiration rate data and/or respiration rate parameters to baseline respiration rate data/parameters for the user. In other words, the system 200 may be configured to generate within user normalized respiration rate data baselines for the user, and may compare subsequent respiration rate data for the user to the user's own baseline data to determine whether the user is likely experiencing medical conditions (e.g., compare respiration rate data to the user's own historical respiration rate data).

For example, the system 200 may continuously collect physiological data from a user to determine baseline respiration rate data for the user (e.g., baseline respiration rate values, baseline respiration rate parameters). The system 200 may then compare subsequently-received respiration rate data and/or respiration rate parameters to the user's baseline respiration rate data to determine condition risk metrics for the user. In this example, deviations from the user's baseline respiration rate data may be indicative of a higher relative probability that the user is experiencing (or is likely to experience in the future) some medical condition.

In some implementations, a computing device of the system 200 may determine a relationship between time series data of respiration rate and sleep stage transitions or other parameters within a user, with the notion that illness or physiologic strain may disrupt physiological parameters that underlie healthy and restorative physiologic processes during sleep (e.g., determine respiration rate parameters conditioned on sleep stages or sleep stage transitions). In particular, the system 200 may compare determined respiration rate values/parameters to certain classified sleep periods for the user (e.g., REM sleep periods, light sleep periods, deep sleep periods) in order to determine the condition risk metrics for the user.

For example, the system 200 may collect physiological data for the user over a night of sleep, and may classify the night of sleep into different sleep periods, including awake sleep periods, light sleep periods, REM sleep periods, and deep sleep periods. In this example, the system 200 may then determine condition risk metrics for the user based on the user's respiration rate values/parameters within or across specific classified sleep periods. For instance, in some cases, the system 200 may evaluate how the user's respiration rate changed across REM sleep periods over the night (e.g., respiration rate parameters determined only based on REM sleep periods). In other words, in some implementations, the system 200 may evaluate the user's respiration rate with respect to the user's classified sleep periods in order to determine whether or not the user is experiencing medical conditions.

In some aspects, the system 200 may be configured to report respiration rate values, respiration rate parameters, and/or determined condition risk metrics to the user, which may provide the user with a more comprehensive view of their sleeping patterns and overall health. This may be further shown and described with reference to FIG. 5.

Figure 5:
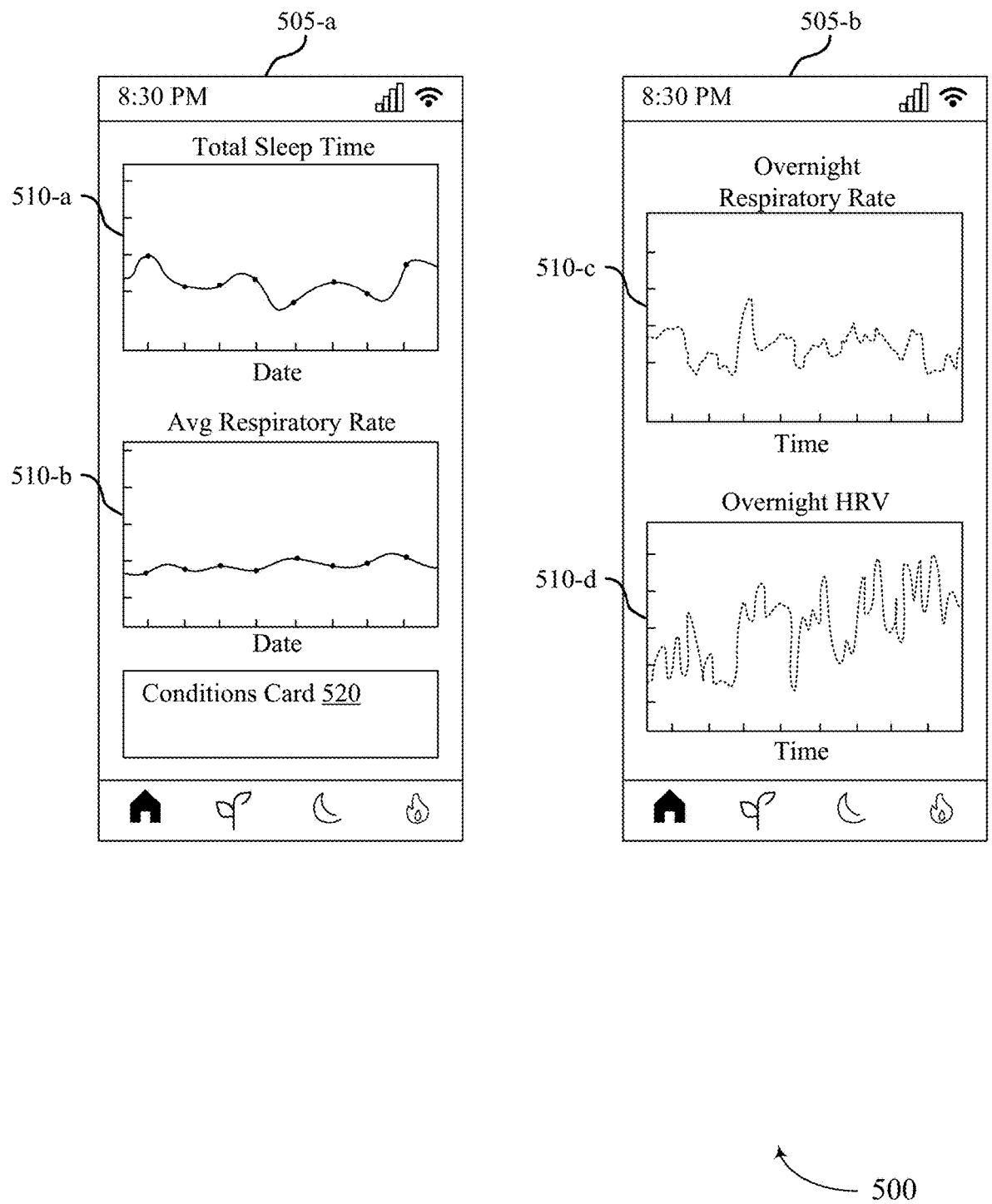
FIG. 5 illustrates an example of a graphical user interface (GUI) that supports identifying conditions using respiration rate in accordance with aspects of the present disclosure.

FIG. 5 illustrates an example of a GUI 500 that supports identifying conditions using respiration rate in accordance with aspects of the present disclosure. The GUI 500 may implement, or be implemented by, aspects of the system 100, system 200, respiration rate diagram 300, respiration rate diagram 400, or any combination thereof. For example, the GUI 500 may include an example of the GUI 275 included within the user device 106 illustrated in FIG. 2.

The GUI 500 illustrates a series of application pages 505 which may be displayed to the user via the GUI 500 (e.g., GUI 275 illustrated in FIG. 2). The application page 505-*a* illustrates a user's total sleep time in relation to the user's average respiration rate over some time period, such as a week or month. In some cases, the system 200 may calculate a single, average respiration rate value for each respective day within the time interval (e.g., over the course of a month), and may display the daily average respiration rate values via an average respiration rate graph 510-*b*. In this regard, the average respiration rate graph 510-*b* illustrates how the user's average respiration rate has changed over the course of a week or month (or some other selected time duration). Similarly, the system 200 may calculate and display a single total sleep time value for each respective day, and may display the total sleep time values via a total sleep time graph 510-*a*.

By comparing the total sleep time graph 510-*a* and the average respiration rate graph 510-*b*, a user may be able to quickly see how their respiration rates are affected by their total sleep time. For example, comparison of the total sleep time graph 510-*a* and the average respiration rate graph 510-*b* may indicate that preceding nights of inadequate sleep may yield subsequent nights of sleep with more elevated respiration rate averages. In some implementations, the GUI 500 may report correlations (e.g., Spearmann correlations) on the total sleep time graph 510-*a* and/or the average respiration rate graph 510-*b* which indicate correlations between the user's total sleep and respiration rates. For example, the GUI 500 may indicate an average respiration rate for the user for days following nights in which the user experienced less than seven hours of sleep (e.g., "Your average respiration rate following a night of less than 7 hours of sleep is x.").

The application page 505-*b* illustrates a user's continuous respiration rate values over time in relation to the user's HRV values. For example, the overnight respiration rate graph 510-c illustrates continuous respiration rate values for the user over a night of sleep, and the overnight HRV graph 510-d illustrates continuous HRV values for the user over the night of sleep. As described previously herein, the respiration rate values and the HRV values of the respiration rate graph 510-c and the overnight HRV graph 510-d, respectively, may be determined and displayed according to regular or irregular periodicities (e.g., one measurement per thirty seconds, one measurement per minute, one measurement per five minutes). The information on application page 505-b may enable users to see how their respiration rate changes over some time period, such as over a night of sleep or over the course of a 24-hour day, and may enable users to see a relationship between their respiration rate and other physiological parameters such as HRV and temperature. Moreover, in cases where the user's continuous respiration rate is displayed over the course of a day, users may be able to view how exercise affects their respiration rate, and how their respiration rate recovers following exercise.

In some implementations, by displaying the users' respiration rate and/or respiration rate parameters via the GUI 500, the system 200 may enable users to identify and/or manage other conditions characterized by respiratory challenges or distress, such as asthma, allergies, sleep deprivation, and the like. In some implementations, the system 200 may provide users with reports that include respiration rate data and various conclusions/recommendations. For example, the application page 505-a may include a card 520 (and/or additional application pages 505) which is configured to display graphics, curves, summary values, and/or conclusions/recommendations associated with a user's respiration rate and/or respiration rate parameters.

In some aspects, the system 200 may display determined condition risk metrics to the user via the GUI 500 (e.g., GUI 275 of user device 106) via the card 520. For example, upon generating a condition risk metric which is associated with a relatively high probability that the user is experiencing sleep deprivation, the card 520 may display an alert or message which indicates that the user may be experiencing sleep deprivation. In some aspects, the system 200 may provide information as to why the system 200 has identified potential medical conditions, as well as insights or other information as to how the user may modify their behaviors to address identified medical conditions or reduce a likelihood that the user will experience identified medical conditions. The users may use the data included in generated alerts and messages to make behavioral decisions, such as modifying their schedule to include more sleep in response to a notice that they may be sleep deprived, or engaging in certain breathing exercises intended to enhance parasympathetic activation, a modulator of respiration rate.

For example, in cases where the user may be sleep deprived, the system 200 may cause the card 520 to display a recommendation that the user modify their sleep patterns to modify/improve their condition. Similarly, if the system 200 is aware of other underlying user conditions (e.g., asthma, sleep apnea, allergies, COPD, etc.), the underlying conditions may trigger an alert or message that notifies the user of their respiration rate parameters, and provides recommendations to address the issue. Example recommendations may include behavior changes, visiting a doctor, etc.

Figure 6:
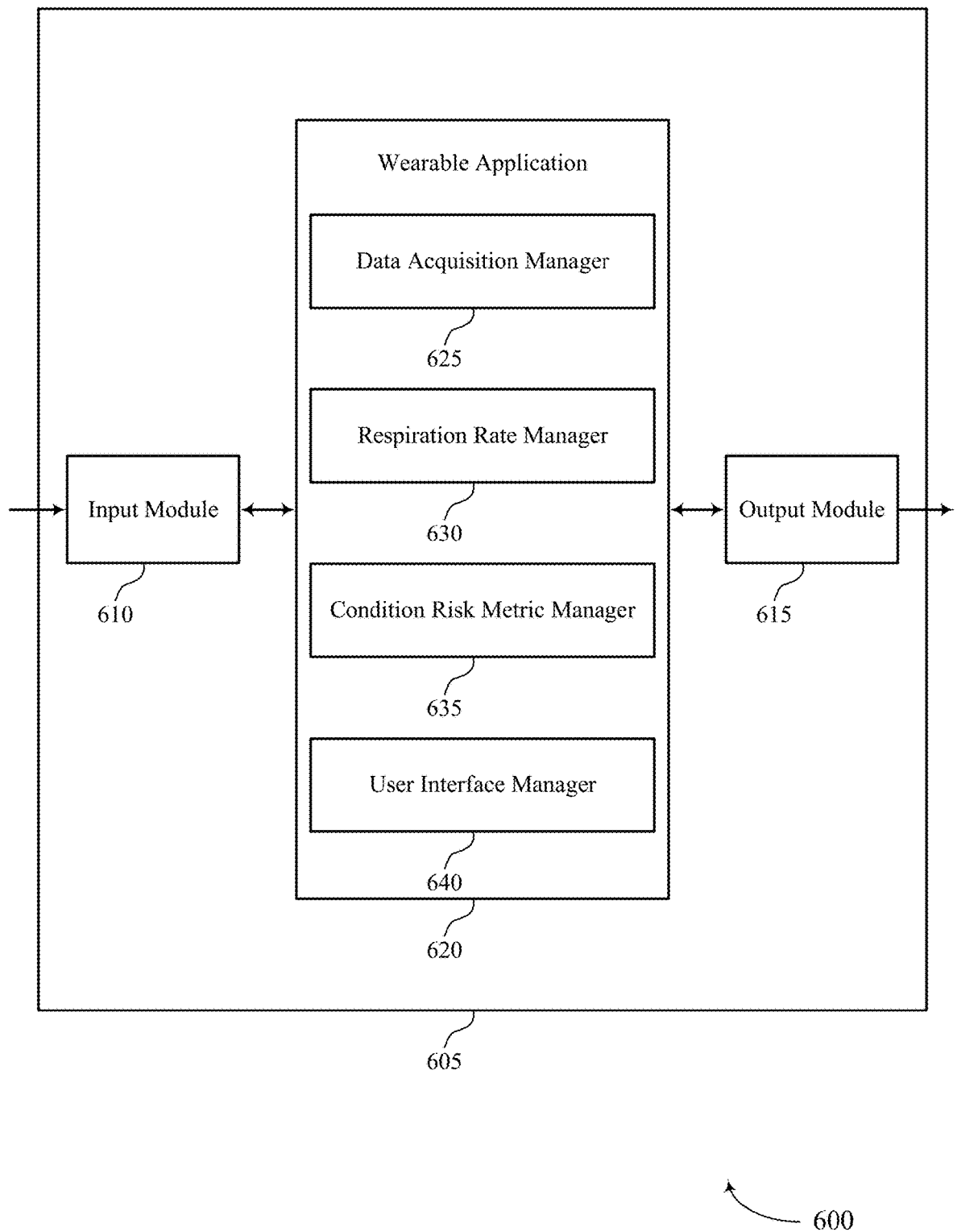
FIG. 6 shows a block diagram of an apparatus that supports identifying conditions using respiration rate in accordance with aspects of the present disclosure.

FIG. 6 shows a block diagram 600 of a device 605 that supports identifying conditions using respiration rate in accordance with aspects of the present disclosure. The device 605 may include an input module 610, an output module 615, and a wearable application 620. The device 605 may also include a processor. Each of these components may be in communication with one another (e.g., via one or more buses).

The input module 610 may provide a means for receiving information such as packets, user data, control information, or any combination thereof associated with various information channels (e.g., control channels, data channels, information channels related to illness detection techniques). Information may be passed on to other components of the device 605. The input module 610 may utilize a single antenna or a set of multiple antennas.

The output module 615 may provide a means for transmitting signals generated by other components of the device 605. For example, the output module 615 may transmit information such as packets, user data, control information, or any combination thereof associated with various information channels (e.g., control channels, data channels, information channels related to illness detection techniques). In some examples, the output module 615 may be co-located with the input module 610 in a transceiver module. The output module 615 may utilize a single antenna or a set of multiple antennas.

For example, the wearable application 620 may include a data acquisition manager 625, a respiration rate manager 630, a condition risk metric manager 635, a user interface manager 640, or any combination thereof. In some examples, the wearable application 620, or various components thereof, may be configured to perform various operations (e.g., receiving, monitoring, transmitting) using or otherwise in cooperation with the input module 610, the output module 615, or both. For example, the wearable application 620 may receive information from the input module 610, send information to the output module 615, or be integrated in combination with the input module 610, the output module 615, or both to receive information, transmit information, or perform various other operations as described herein.

The data acquisition manager 625 may be configured as or otherwise support a means for receiving physiological data associated with a user, the physiological data being continuously collected via a wearable device associated with the user. The respiration rate manager 630 may be configured as or otherwise support a means for determining a plurality of respiration rate values for the user over a time interval based at least in part on the physiological data. The respiration rate manager 630 may be configured as or otherwise support a means for determining one or more respiration rate parameters associated with a change in the plurality of respiration rate values over the time interval. The condition risk metric manager 635 may be configured as or otherwise support a means for determining one or more condition risk metrics associated with one or more medical conditions based at least in part on the one or more respiration rate parameters, the one or more condition risk metrics associated with a relative probability that the user is associated with a respective medical condition of the one or more medical conditions. The user interface manager 640 may be configured as or otherwise support a means for causing a GUI of a user device to display an indication of the one or more condition risk metrics.

Figure 7:
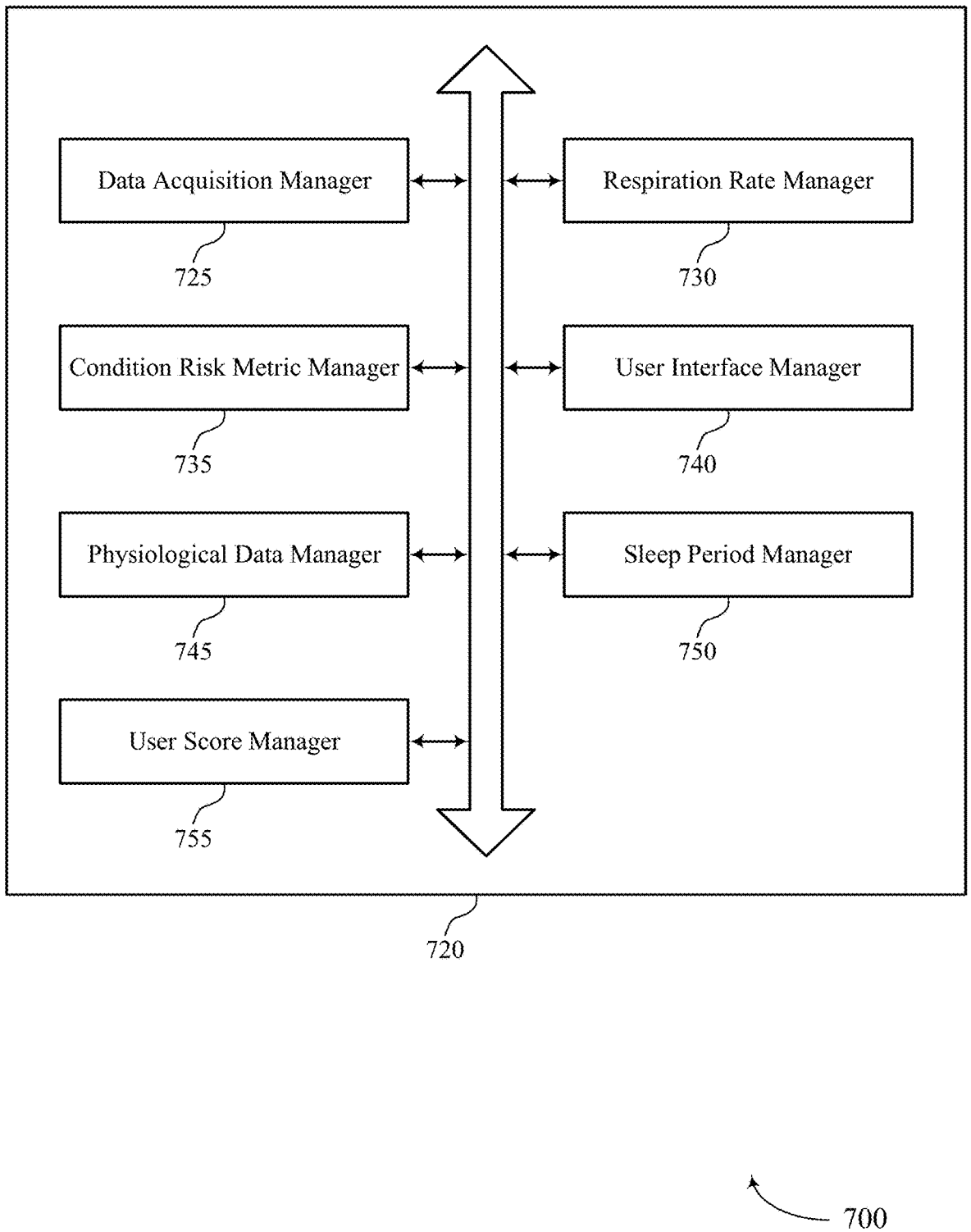
FIG. 7 shows a block diagram of a wearable application that supports identifying conditions using respiration rate in accordance with aspects of the present disclosure.

FIG. 7 shows a block diagram 700 of a wearable application 720 that supports identifying conditions using respiration rate in accordance with aspects of the present disclosure. The wearable application 720 may be an example of aspects of a wearable application or a wearable application 620, or both, as described herein. The wearable application 720, or various components thereof, may be an example of means for performing various techniques for identifying conditions using respiration rate as described herein. For example, the wearable application 720 may include a data acquisition manager 725, a respiration rate manager 730, a condition risk metric manager 735, a user interface manager 740, a physiological data manager 745, a sleep period manager 750, a user score manager 755, or any combination thereof. Each of these components may communicate, directly or indirectly, with one another (e.g., via one or more buses).

The data acquisition manager 725 may be configured as or otherwise support a means for receiving physiological data associated with a user, the physiological data being continuously collected via a wearable device associated with the user. The respiration rate manager 730 may be configured as or otherwise support a means for determining a plurality of respiration rate values for the user over a time interval based at least in part on the physiological data. In some examples, the respiration rate manager 730 may be configured as or otherwise support a means for determining one or more respiration rate parameters associated with a change in the plurality of respiration rate values over the time interval. The condition risk metric manager 735 may be configured as or otherwise support a means for determining one or more condition risk metrics associated with one or more medical conditions based at least in part on the one or more respiration rate parameters, the one or more condition risk metrics associated with a relative probability that the user is associated with a respective medical condition of the one or more medical conditions. The user interface manager 740 may be configured as or otherwise support a means for causing a GUI of a user device to display an indication of the one or more condition risk metrics.

In some examples, the respiration rate manager 730 may be configured as or otherwise support a means for fitting a line to the plurality of respiration rate values for the user over the time interval. In some examples, the respiration rate manager 730 may be configured as or otherwise support a means for determining a slope of the line, wherein the one or more respiration rate parameters comprise the slope, and wherein determining the one or more condition risk metrics is based at least in part on the slope.

In some examples, the condition risk metric manager 735 may be configured as or otherwise support a means for determining a first condition risk metric for a medical condition of the one or more medical conditions based at least in part on the slope being greater than a threshold slope value. In some examples, the condition risk metric manager 735 may be configured as or otherwise support a means for determining a second condition risk metric for the medical condition based at least in part on the slope being less than the threshold slope value, the second condition risk metric different from the first condition risk metric. In some examples, the medical condition comprises sleep deprivation. In some examples, the first condition risk metric is associated with a higher relative probability of sleep deprivation compared to the second condition risk metric.

In some examples, the physiological data manager 745 may be configured as or otherwise support a means for determining one or more parameters of the physiological data collected during the time interval, wherein determining the one or more condition risk metrics is based at least in part on the plurality of respiration rate values and the one or more parameters of the physiological data.

In some examples, the data acquisition manager 725 may be configured as or otherwise support a means for receiving additional physiological data associated with the user, the additional physiological data being continuously collected via the wearable device over an additional time interval which precedes the time interval. In some examples, the respiration rate manager 730 may be configured as or otherwise support a means for determining baseline respiration rate data for the user based at least in part on the additional physiological data, wherein determining the plurality of respiration rate values, the one or more respiration rate parameters, the one or more condition risk metrics, or any combination thereof, is based at least in part on the baseline respiration rate data.

In some examples, the sleep period manager 750 may be configured as or otherwise support a means for determining one or more sleep periods for the user within the time interval based at least in part on the physiological data. In some examples, the sleep period manager 750 may be configured as or otherwise support a means for classifying each sleep period of the one or more sleep periods into at least one of an awake sleep period, a light sleep period, a REM sleep period, or a deep sleep period, wherein determining the one or more condition risk metrics is based at least in part on the one or more respiration rate parameters and the one or more classified sleep periods.

In some examples, the user interface manager 740 may be configured as or otherwise support a means for causing the GUI of the user device to display a graph indicating the plurality of respiration rate values over the time interval.

In some examples, the user score manager 755 may be configured as or otherwise support a means for determining one or more scores for the user based at least in part on the plurality of respiration rate values, the one or more respiration rate parameters, or both, the one or more scores comprising a sleep score, a readiness score, or both.

In some examples, the time interval comprises a night of sleep for the user. In some examples, the one or more respiration rate parameters comprise a rate of change in the plurality of respiration rate values over the time interval, a total change in the plurality of respiration rate values over the time interval, a relationship between the plurality of respiration rate values and one or more classified sleep periods for the user within the time interval, or any combination thereof.

In some examples, the one or more medical conditions comprise sleep deprivation, sleep apnea, asthma, allergies, COPD, lung damage, or any combination thereof. In some examples, the wearable device comprises a wearable ring device. In some examples, the wearable device collects the physiological data from the user based on arterial blood flow.

Figure 8:
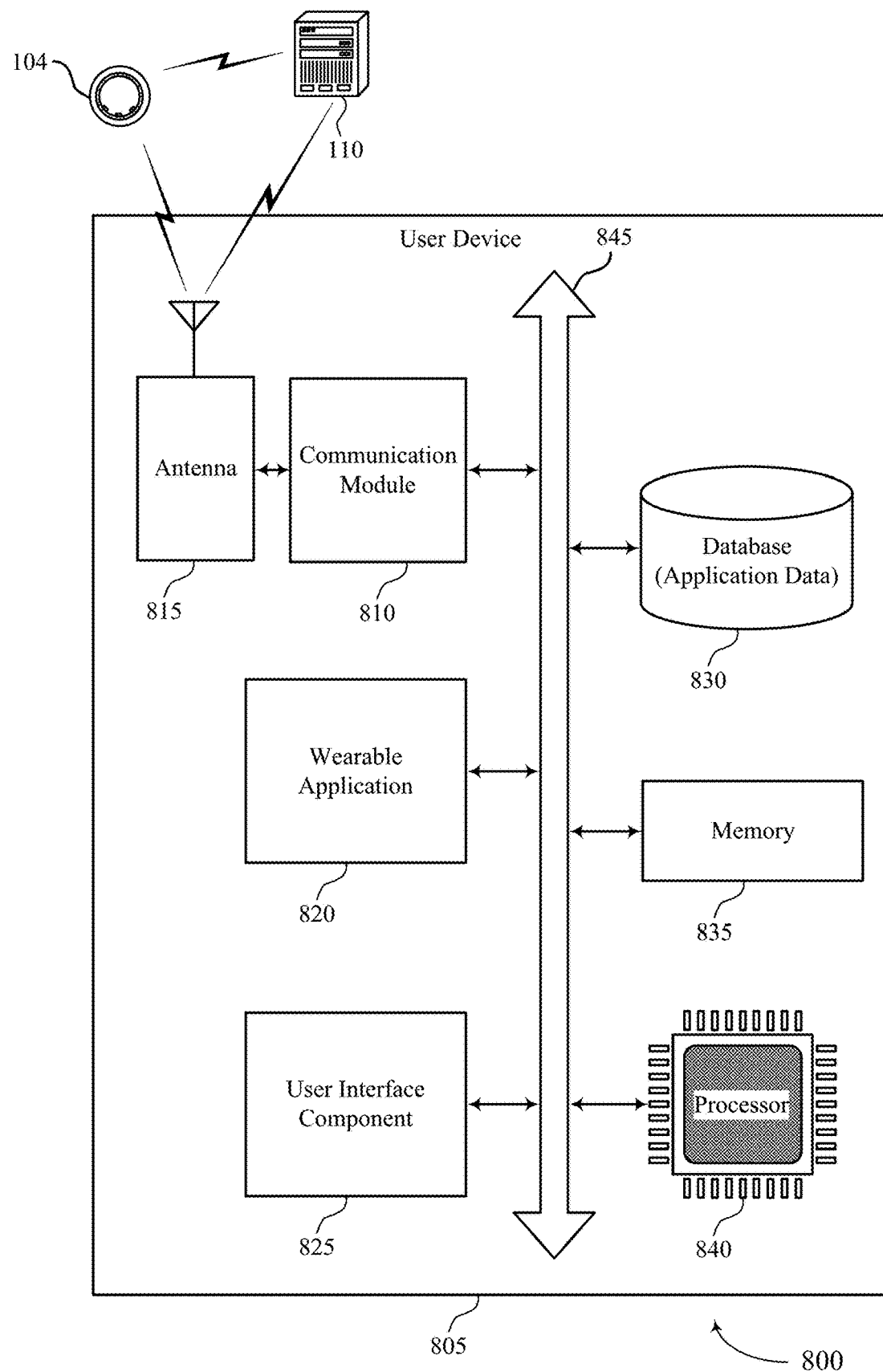
FIG. 8 shows a diagram of a system including a device that supports identifying conditions using respiration rate in accordance with aspects of the present disclosure.

FIG. 8 shows a diagram of a system 800 including a device 805 that supports identifying conditions using respiration rate in accordance with aspects of the present disclosure. The device 805 may be an example of or include the components of a device 605 as described herein. In some implementations, the device 805 may include an example of a user device 106 described herein. The device 805 may include components for bi-directional communications with a wearable device (e.g., ring 104) and a server 110, such as a wearable application 820, a communication module 810, an antenna 815, a user interface component 825, a database (application data) 830, a memory 835, and a processor 840. These components may be in electronic communication or otherwise coupled (e.g., operatively, communicatively, functionally, electronically, electrically) via one or more buses (e.g., a bus 845).

The communication module 810 may manage input and output signals for the device 805 via the antenna 815. The communication module 810 may include an example of the communication module 220-b of the user device 106 shown and described in FIG. 2. In this regard, the communication module 810 may manage communications with the ring 104 and the server 110, as illustrated in FIG. 2. The communication module 810 may also manage peripherals not integrated into the device 805. In some cases, the communication module 810 may represent a physical connection or port to an external peripheral. In some cases, the communication module 810 may utilize an operating system such as iOS®, ANDROID®, MS-DOS®, MS-WINDOWS®, OS/2®, UNIX®, LINUX®, or another known operating system. In other cases, the communication module 810 may represent or interact with a wearable device (e.g., ring 104), modem, a keyboard, a mouse, a touchscreen, or a similar device. In some cases, the communication module 810 may be implemented as part of the processor 840. In some examples, a user may interact with the device 805 via the communication module 810, user interface component 825, or via hardware components controlled by the communication module 810.

In some cases, the device 805 may include a single antenna 815. However, in some other cases, the device 805 may have more than one antenna 815, which may be capable of concurrently transmitting or receiving multiple wireless transmissions. The communication module 810 may communicate bi-directionally, via the one or more antennas 815, wired, or wireless links as described herein. For example, the communication module 810 may represent a wireless transceiver and may communicate bi-directionally with another wireless transceiver. The communication module 810 may also include a modem to modulate the packets, to provide the modulated packets to one or more antennas 815 for transmission, and to demodulate packets received from the one or more antennas 815.

The user interface component 825 may manage data storage and processing in a database 830. In some cases, a user may interact with the user interface component 825. In other cases, the user interface component 825 may operate automatically without user interaction. The database 830 may be an example of a single database, a distributed database, multiple distributed databases, a data store, a data lake, or an emergency backup database.

The memory 835 may include RAM and ROM. The memory 835 may store computer-readable, computer-executable software including instructions that, when executed, cause the processor 840 to perform various functions described herein. In some cases, the memory 835 may contain, among other things, a basic I/O system (BIOS) which may control basic hardware or software operation such as the interaction with peripheral components or devices.

The processor 840 may include an intelligent hardware device, (e.g., a general-purpose processor, a digital signal processor (DSP), a central processing unit (CPU), a microcontroller, an application-specific integrated circuit (ASIC), a field-programmable gate array (FPGA), a programmable logic device, a discrete gate or transistor logic component, a discrete hardware component, or any combination thereof). In some cases, the processor 840 may be configured to operate a memory array using a memory controller. In other cases, a memory controller may be integrated into the processor 840. The processor 840 may be configured to execute computer-readable instructions stored in a memory 835 to perform various functions (e.g., functions or tasks supporting a method and system for sleep staging algorithms).

For example, the wearable application 820 may be configured as or otherwise support a means for receiving physiological data associated with a user, the physiological data being continuously collected via a wearable device associated with the user. The wearable application 820 may be configured as or otherwise support a means for determining a plurality of respiration rate values for the user over a time interval based at least in part on the physiological data. The wearable application 820 may be configured as or otherwise support a means for determining one or more respiration rate parameters associated with a change in the plurality of respiration rate values over the time interval. The wearable application 820 may be configured as or otherwise support a means for determining one or more condition risk metrics associated with one or more medical conditions based at least in part on the one or more respiration rate parameters, the one or more condition risk metrics associated with a relative probability that the user is associated with a respective medical condition of the one or more medical conditions. The wearable application 820 may be configured as or otherwise support a means for causing a GUI of a user device to display an indication of the one or more condition risk metrics.

The wearable application 820 may include an application (e.g., "app"), program, software, or other component which is configured to facilitate communications with a ring 104, server 110, other user devices 106, and the like. For example, the wearable application 820 may include an application executable on a user device 106 which is configured to receive data (e.g., physiological data) from a ring 104, perform processing operations on the received data, transmit and receive data with the servers 110, and cause presentation of data to a user 102.

Figure 9:
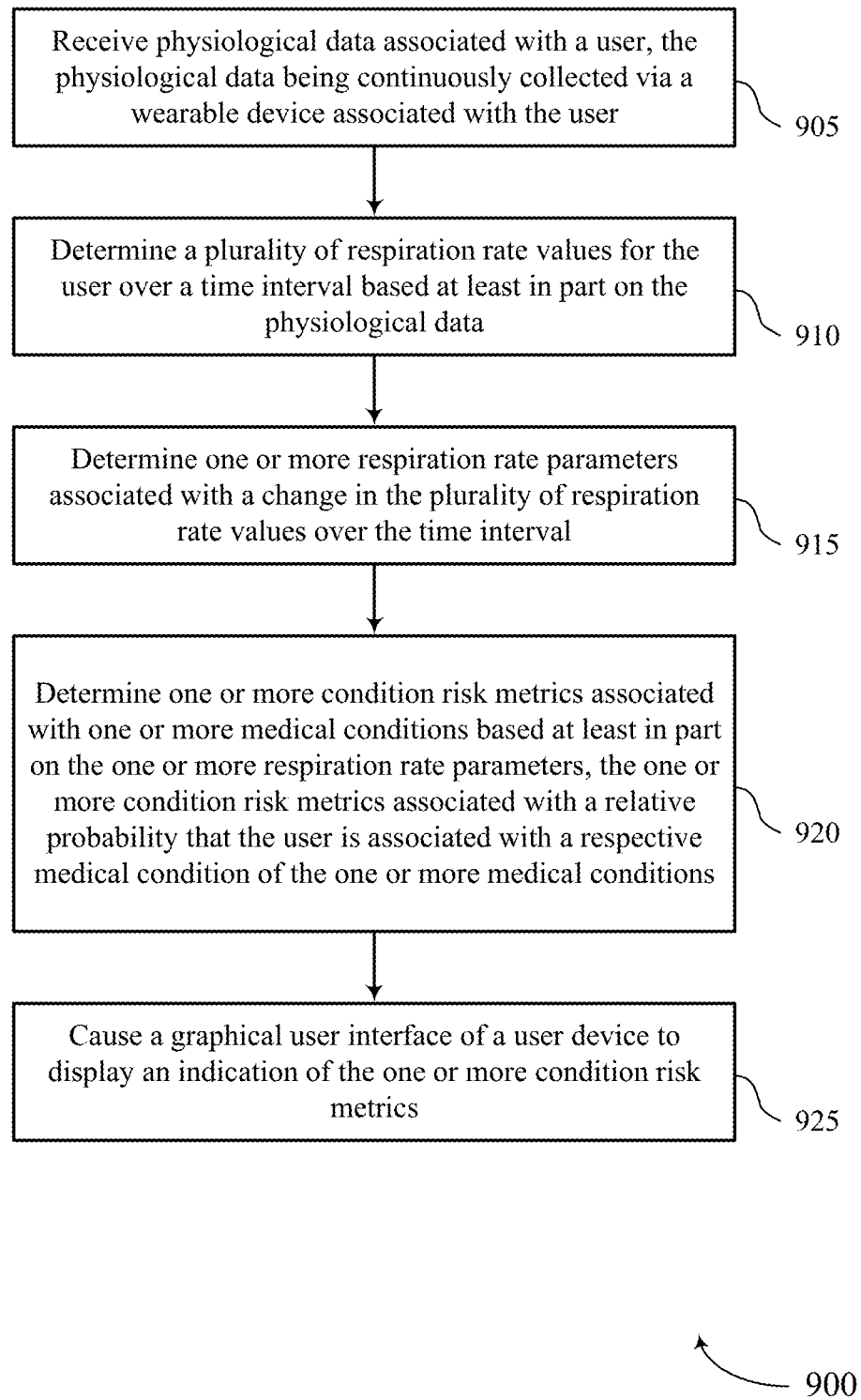
FIGS. 9 through 11 show flowcharts illustrating methods that support identifying conditions using respiration rate in accordance with aspects of the present disclosure.

FIG. 9 shows a flowchart illustrating a method 900 that supports identifying conditions using respiration rate in accordance with aspects of the present disclosure. The operations of the method 900 may be implemented by a user device or its components as described herein. For example, the operations of the method 900 may be performed by a user device as described with reference to FIGS. 1 through 8. In some examples, a user device may execute a set of instructions to control the functional elements of the user device to perform the described functions. Additionally or alternatively, the user device may perform aspects of the described functions using special-purpose hardware.

At 905, the method may include receiving physiological data associated with a user, the physiological data being continuously collected via a wearable device associated with the user. The operations of 905 may be performed in accordance with examples as disclosed herein. In some examples, aspects of the operations of 905 may be performed by a data acquisition manager 725 as described with reference to FIG. 7.

At 910, the method may include determining a plurality of respiration rate values for the user over a time interval based at least in part on the physiological data. The operations of 910 may be performed in accordance with examples as disclosed herein. In some examples, aspects of the operations of 910 may be performed by a respiration rate manager 730 as described with reference to FIG. 7.

At 915, the method may include determining one or more respiration rate parameters associated with a change in the plurality of respiration rate values over the time interval. The operations of 915 may be performed in accordance with examples as disclosed herein. In some examples, aspects of the operations of 915 may be performed by a respiration rate manager 730 as described with reference to FIG. 7.

At 920, the method may include determining one or more condition risk metrics associated with one or more medical conditions based at least in part on the one or more respiration rate parameters, the one or more condition risk metrics associated with a relative probability that the user is associated with a respective medical condition of the one or more medical conditions. The operations of 920 may be performed in accordance with examples as disclosed herein. In some examples, aspects of the operations of 920 may be performed by a condition risk metric manager 735 as described with reference to FIG. 7.

At 925, the method may include causing a GUI of a user device to display an indication of the one or more condition risk metrics. The operations of 925 may be performed in accordance with examples as disclosed herein. In some examples, aspects of the operations of 925 may be performed by a user interface manager 740 as described with reference to FIG. 7.

Figure 10:
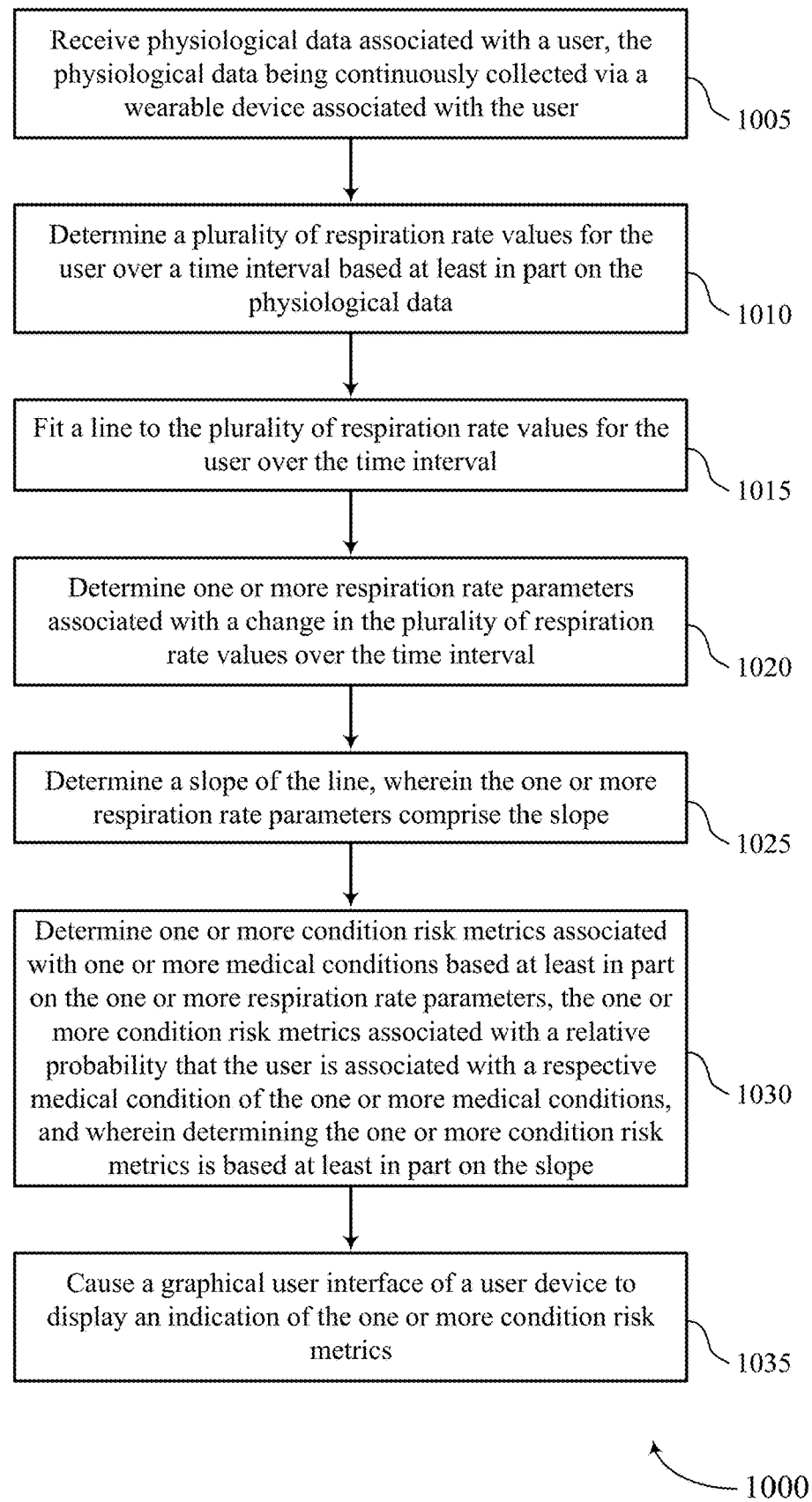

FIG. 10 shows a flowchart illustrating a method 1000 that supports identifying conditions using respiration rate in accordance with aspects of the present disclosure. The operations of the method 1000 may be implemented by a user device or its components as described herein. For example, the operations of the method 1000 may be performed by a user device as described with reference to FIGS. 1 through 8. In some examples, a user device may execute a set of instructions to control the functional elements of the user device to perform the described functions. Additionally or alternatively, the user device may perform aspects of the described functions using special-purpose hardware.

At 1005, the method may include receiving physiological data associated with a user, the physiological data being continuously collected via a wearable device associated with the user. The operations of 1005 may be performed in accordance with examples as disclosed herein. In some examples, aspects of the operations of 1005 may be performed by a data acquisition manager 725 as described with reference to FIG. 7.

At 1010, the method may include determining a plurality of respiration rate values for the user over a time interval based at least in part on the physiological data. The operations of 1010 may be performed in accordance with examples as disclosed herein. In some examples, aspects of the operations of 1010 may be performed by a respiration rate manager 730 as described with reference to FIG. 7.

At 1015, the method may include fitting a line to the plurality of respiration rate values for the user over the time interval. The operations of 1015 may be performed in accordance with examples as disclosed herein. In some examples, aspects of the operations of 1015 may be performed by a respiration rate manager 730 as described with reference to FIG. 7.

At 1020, the method may include determining one or more respiration rate parameters associated with a change in the plurality of respiration rate values over the time interval. The operations of 1020 may be performed in accordance with examples as disclosed herein. In some examples, aspects of the operations of 1020 may be performed by a respiration rate manager 730 as described with reference to FIG. 7.

At 1025, the method may include determining a slope of the line, wherein the one or more respiration rate parameters comprise the slope, and wherein determining the one or more condition risk metrics is based at least in part on the slope. The operations of 1025 may be performed in accordance with examples as disclosed herein. In some examples, aspects of the operations of 1025 may be performed by a respiration rate manager 730 as described with reference to FIG. 7.

At 1030, the method may include determining one or more condition risk metrics associated with one or more medical conditions based at least in part on the one or more respiration rate parameters, the one or more condition risk metrics associated with a relative probability that the user is associated with a respective medical condition of the one or more medical conditions, and wherein determining the one or more condition risk metrics is based at least in part on the slope. The operations of 1030 may be performed in accordance with examples as disclosed herein. In some examples, aspects of the operations of 1030 may be performed by a condition risk metric manager 735 as described with reference to FIG. 7.

At 1035, the method may include causing a GUI of a user device to display an indication of the one or more condition risk metrics. The operations of 1035 may be performed in accordance with examples as disclosed herein. In some examples, aspects of the operations of 1035 may be performed by a user interface manager 740 as described with reference to FIG. 7.

Figure 11:
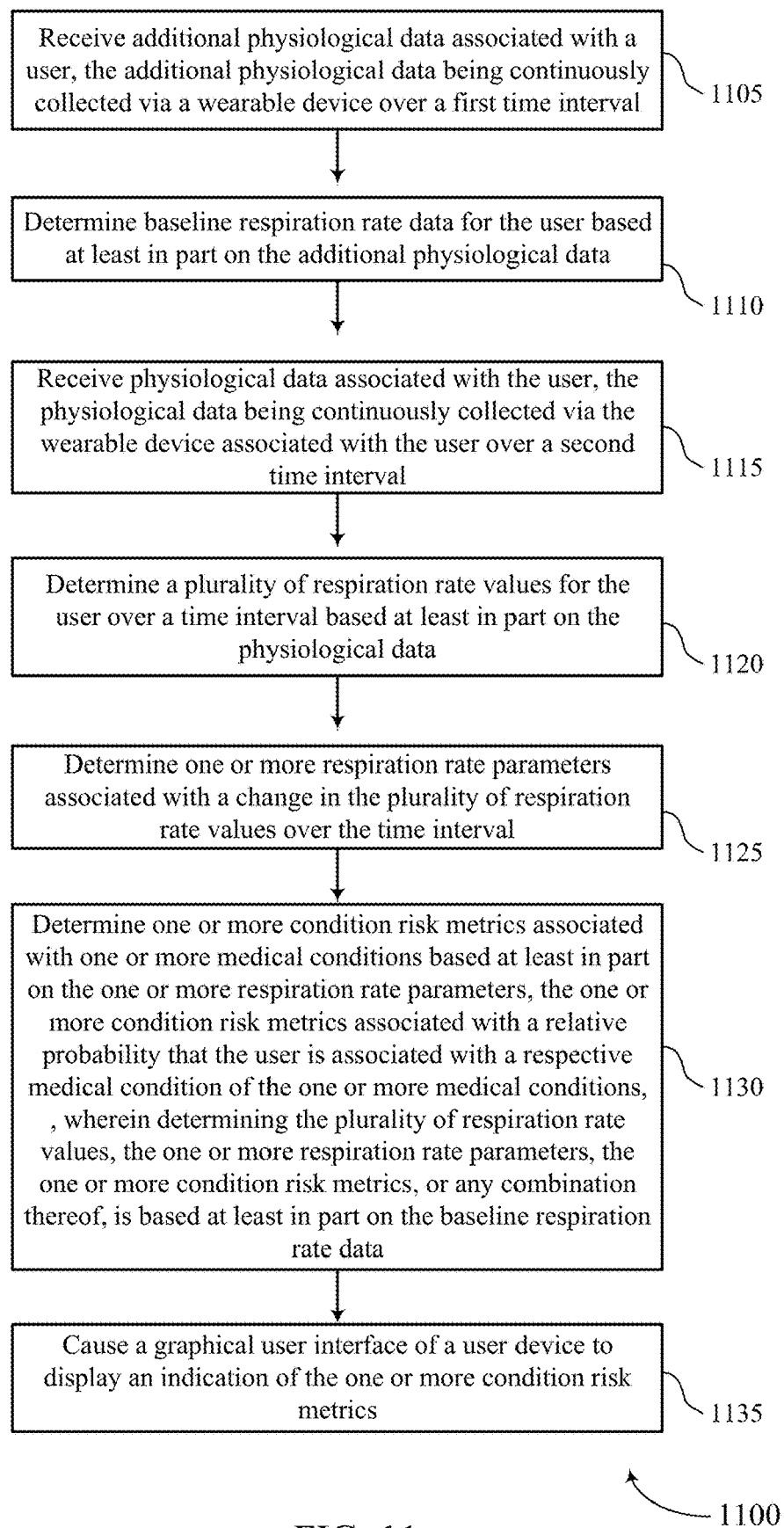

FIG. 11 shows a flowchart illustrating a method 1100 that supports identifying conditions using respiration rate in accordance with aspects of the present disclosure. The operations of the method 1100 may be implemented by a user device or its components as described herein. For example, the operations of the method 1100 may be performed by a user device as described with reference to FIGS. 1 through 8. In some examples, a user device may execute a set of instructions to control the functional elements of the user device to perform the described functions. Additionally or alternatively, the user device may perform aspects of the described functions using special-purpose hardware.

At 1105, the method may include receiving additional physiological data associated with a user, the additional physiological data being continuously collected via a wearable device over a first time interval. The operations of 1105 may be performed in accordance with examples as disclosed herein. In some examples, aspects of the operations of 1105 may be performed by a data acquisition manager 725 as described with reference to FIG. 7.

At 1110, the method may include determining baseline respiration rate data for the user based at least in part on the additional physiological data. The operations of 1110 may be performed in accordance with examples as disclosed herein. In some examples, aspects of the operations of 1110 may be performed by a respiration rate manager 730 as described with reference to FIG. 7.

At 1115, the method may include receiving physiological data associated with the user, the physiological data being continuously collected via the wearable device associated with the user over a second time interval. The operations of 1115 may be performed in accordance with examples as disclosed herein. In some examples, aspects of the operations of 1115 may be performed by a data acquisition manager 725 as described with reference to FIG. 7.

At 1120, the method may include determining a plurality of respiration rate values for the user over a time interval based at least in part on the physiological data. The operations of 1120 may be performed in accordance with examples as disclosed herein. In some examples, aspects of the operations of 1120 may be performed by a respiration rate manager 730 as described with reference to FIG. 7.

At 1125, the method may include determining one or more respiration rate parameters associated with a change in the plurality of respiration rate values over the time interval. The operations of 1125 may be performed in accordance with examples as disclosed herein. In some examples, aspects of the operations of 1125 may be performed by a respiration rate manager 730 as described with reference to FIG. 7.

At 1130, the method may include determining one or more condition risk metrics associated with one or more medical conditions based at least in part on the one or more respiration rate parameters, the one or more condition risk metrics associated with a relative probability that the user is associated with a respective medical condition of the one or more medical conditions, wherein determining the plurality of respiration rate values, the one or more respiration rate parameters, the one or more condition risk metrics, or any combination thereof, is based at least in part on the baseline respiration rate data. The operations of 1130 may be performed in accordance with examples as disclosed herein. In some examples, aspects of the operations of 1130 may be performed by a condition risk metric manager 735 as described with reference to FIG. 7.

At 1135, the method may include causing a GUI of a user device to display an indication of the one or more condition risk metrics. The operations of 1135 may be performed in accordance with examples as disclosed herein. In some examples, aspects of the operations of 1135 may be performed by a user interface manager 740 as described with reference to FIG. 7.

A method is described. The method may include receiving physiological data associated with a user, the physiological data being continuously collected via a wearable device associated with the user, determining a plurality of respiration rate values for the user over a time interval based at least in part on the physiological data, determining one or more respiration rate parameters associated with a change in the plurality of respiration rate values over the time interval, determining one or more condition risk metrics associated with one or more medical conditions based at least in part on the one or more respiration rate parameters, the one or more condition risk metrics associated with a relative probability that the user is associated with a respective medical condition of the one or more medical conditions, and causing a GUI of a user device to display an indication of the one or more condition risk metrics.

An apparatus is described. The apparatus may include a processor, memory coupled with the processor, and instructions stored in the memory. The instructions may be executable by the processor to cause the apparatus to receive physiological data associated with a user, the physiological data being continuously collected via a wearable device associated with the user, determine a plurality of respiration rate values for the user over a time interval based at least in part on the physiological data, determine one or more respiration rate parameters associated with a change in the plurality of respiration rate values over the time interval, determine one or more condition risk metrics associated with one or more medical conditions based at least in part on the one or more respiration rate parameters, the one or more condition risk metrics associated with a relative probability that the user is associated with a respective medical condition of the one or more medical conditions, and cause a GUI of a user device to display an indication of the one or more condition risk metrics.

Another apparatus is described. The apparatus may include means for receiving physiological data associated with a user, the physiological data being continuously collected via a wearable device associated with the user, means for determining a plurality of respiration rate values for the user over a time interval based at least in part on the physiological data, means for determining one or more respiration rate parameters associated with a change in the plurality of respiration rate values over the time interval, means for determining one or more condition risk metrics associated with one or more medical conditions based at least in part on the one or more respiration rate parameters, the one or more condition risk metrics associated with a relative probability that the user is associated with a respective medical condition of the one or more medical conditions, and means for causing a GUI of a user device to display an indication of the one or more condition risk metrics.

A non-transitory computer-readable medium storing code is described. The code may include instructions executable by a processor to receive physiological data associated with a user, the physiological data being continuously collected via a wearable device associated with the user, determine a plurality of respiration rate values for the user over a time interval based at least in part on the physiological data, determine one or more respiration rate parameters associated with a change in the plurality of respiration rate values over the time interval, determine one or more condition risk metrics associated with one or more medical conditions based at least in part on the one or more respiration rate parameters, the one or more condition risk metrics associated with a relative probability that the user is associated with a respective medical condition of the one or more medical conditions, and cause a GUI of a user device to display an indication of the one or more condition risk metrics.

Some examples of the method, apparatuses, and non-transitory computer-readable medium described herein may further include operations, features, means, or instructions for fitting a line to the plurality of respiration rate values for the user over the time interval and determining a slope of the line, wherein the one or more respiration rate parameters comprise the slope, and wherein determining the one or more condition risk metrics may be based at least in part on the slope.

Some examples of the method, apparatuses, and non-transitory computer-readable medium described herein may further include operations, features, means, or instructions for determining a first condition risk metric for a medical condition of the one or more medical conditions based at least in part on the slope being greater than a threshold slope value and determining a second condition risk metric for the medical condition based at least in part on the slope being less than the threshold slope value, the second condition risk metric different from the first condition risk metric.

In some examples of the method, apparatuses, and non-transitory computer-readable medium described herein, the medical condition comprises sleep deprivation, and the first condition risk metric may be associated with a higher relative probability of sleep deprivation compared to the second condition risk metric.

Some examples of the method, apparatuses, and non-transitory computer-readable medium described herein may further include operations, features, means, or instructions for determining one or more parameters of the physiological data collected during the time interval, wherein determining the one or more condition risk metrics may be based at least in part on the plurality of respiration rate values and the one or more parameters of the physiological data.

Some examples of the method, apparatuses, and non-transitory computer-readable medium described herein may further include operations, features, means, or instructions for receiving additional physiological data associated with the user, the additional physiological data being continuously collected via the wearable device over an additional time interval which precedes the time interval and determinizing baseline respiration rate data for the user based at least in part on the additional physiological data, wherein determining the plurality of respiration rate values, the one or more respiration rate parameters, the one or more condition risk metrics, or any combination thereof, may be based at least in part on the baseline respiration rate data.

Some examples of the method, apparatuses, and non-transitory computer-readable medium described herein may further include operations, features, means, or instructions for determining one or more sleep periods for the user within the time interval based at least in part on the physiological data and classifying each sleep period of the one or more sleep periods into at least one of an awake sleep period, a light sleep period, a rapid-eye movement sleep period, or a deep sleep period, wherein determining the one or more condition risk metrics may be based at least in part on the one or more respiration rate parameters and the one or more classified sleep periods.

Some examples of the method, apparatuses, and non-transitory computer-readable medium described herein may further include operations, features, means, or instructions for causing the GUI of the user device to display a graph indicating the plurality of respiration rate values over the time interval.

Some examples of the method, apparatuses, and non-transitory computer-readable medium described herein may further include operations, features, means, or instructions for determining one or more scores for the user based at least in part on the plurality of respiration rate values, the one or more respiration rate parameters, or both, the one or more scores comprising a sleep score, a readiness score, or both.

In some examples of the method, apparatuses, and non-transitory computer-readable medium described herein, the time interval comprises a night of sleep for the user.

In some examples of the method, apparatuses, and non-transitory computer-readable medium described herein, the one or more respiration rate parameters comprise a rate of change in the plurality of respiration rate values over the time interval, a total change in the plurality of respiration rate values over the time interval, a relationship between the plurality of respiration rate values and one or more classified sleep periods for the user within the time interval, or any combination thereof.

In some examples of the method, apparatuses, and non-transitory computer-readable medium described herein, the one or more medical conditions comprise sleep deprivation, sleep apnea, asthma, allergies, COPD, lung damage, or any combination thereof.

In some examples of the method, apparatuses, and non-transitory computer-readable medium described herein, the wearable device comprises a wearable ring device.

In some examples of the method, apparatuses, and non-transitory computer-readable medium described herein, the wearable device collects the physiological data from the user based on arterial blood flow.

It should be noted that the methods described above describe possible implementations, and that the operations and the steps may be rearranged or otherwise modified and that other implementations are possible. Furthermore, aspects from two or more of the methods may be combined.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A wearable ring device configured to be worn on a finger of a user, comprising:
    a housing comprising an external housing and an internal housing;
    a plurality of optical components disposed within the housing, the plurality of optical components comprising one or more light-transmitting components and one or more light-receiving components; and
    one or more processors communicatively coupled with the plurality of optical components, the one or more processors configured to:
        obtain one or more measurements of physiological data associated with the user via the plurality of optical components, the physiological data being continuously collected via the wearable ring device;
        determine a plurality of respiration rate values for the user over a time interval based at least in part on the physiological data;
        determine one or more respiration rate parameters associated with a change in the plurality of respiration rate values over the time interval;
        determine one or more condition risk metrics associated with sleep deprivation based at least in part on the one or more respiration rate parameters, the one or more condition risk metrics associated with a relative probability that the user experiences sleep deprivation; and
        transmit, via a short range transmitter of the wearable ring device, one or more signals causing a graphical user interface of a user device to display an indication of the one or more condition risk metrics.

2. The wearable ring device of claim 1, wherein the one or more processors are further configured to cause the wearable ring device to:
    fit a line to the plurality of respiration rate values for the user over the time interval; and
    determine a slope of the line, wherein the one or more respiration rate parameters comprise the slope, and wherein determining the one or more condition risk metrics is based at least in part on the slope.

3. The wearable ring device of claim 2, wherein the one or more processors are further configured to cause the wearable ring device to:
    determine a first condition risk metric associated with sleep deprivation based at least in part on the slope being greater than a threshold slope value; and
    determine a second condition risk metric associated with sleep deprivation based at least in part on the slope being less than the threshold slope value, the second condition risk metric different from the first condition risk metric.

4. The wearable ring device of claim 3, wherein the first condition risk metric is associated with a higher relative probability of sleep deprivation compared to the second condition risk metric.

5. The wearable ring device of claim 1, wherein the one or more processors are further configured to cause the wearable ring device to:
    determine one or more additional parameters of the physiological data collected during the time interval, wherein determining the one or more condition risk metrics is based at least in part on the plurality of respiration rate values and the one or more additional parameters of the physiological data.

6. The wearable ring device of claim 1, wherein the one or more processors are further configured to cause the wearable ring device to:
    obtain one or more measurement of additional physiological data associated with the user via the plurality of optical components, the additional physiological data being continuously collected via the wearable ring device over an additional time interval which precedes the time interval; and
    determine a baseline respiration rate data for the user based at least in part on the additional physiological data, wherein determining the plurality of respiration rate values, the one or more respiration rate parameters, the one or more condition risk metrics, or any combination thereof, is based at least in part on the baseline respiration rate data.

7. The wearable ring device of claim 1, wherein the one or more processors are further configured to cause the wearable ring device to:
    determine one or more sleep periods for the user within the time interval based at least in part on the physiological data; and
    classify each sleep period of the one or more sleep periods into at least one of an awake sleep period, a light sleep period, a rapid-eye movement sleep period, or a deep sleep period, wherein determining the one or more condition risk metrics is based at least in part on the one or more respiration rate parameters and the one or more classified sleep periods.

8. The wearable ring device of claim 1, wherein the one or more processors are further configured to cause the wearable ring device to:
cause the graphical user interface of the user device to display a graph indicating the plurality of respiration rate values over the time interval.

9. The wearable ring device of claim 1, wherein the one or more processors are further configured to cause the wearable ring device to:
determine one or more scores for the user based at least in part on the plurality of respiration rate values, the one or more respiration rate parameters, or both, the one or more scores comprising a sleep score, a readiness score, or both.

10. The wearable ring device of claim 1, wherein the time interval comprises a night of sleep for the user.

11. The wearable ring device of claim 1, wherein the one or more respiration rate parameters comprise a rate of change of the plurality of respiration rate values over the time interval, a total change in the plurality of respiration rate values over the time interval, a relationship between the plurality of respiration rate values and one or more classified sleep periods for the user within the time interval, or any combination thereof.

12. The wearable ring device of claim 1, wherein the wearable ring device collects the physiological data from the user based on arterial blood flow.

* * * * *